US011635387B2

United States Patent
Ikeda

(10) Patent No.: US 11,635,387 B2
(45) Date of Patent: Apr. 25, 2023

(54) OPTICAL IMAGING SYSTEM USING LATERAL ILLUMINATION FOR DIGITAL ASSAYS

(71) Applicant: Abbott Japan LLC, Tokyo (JP)

(72) Inventor: Tomohiro Ikeda, Matsudo (JP)

(73) Assignee: ABBOTT JAPAN CO., LTD, Chiba Prefecture (JP)

( * ) Notice: Subject to any disclaimer, the term of this patent is extended or adjusted under 35 U.S.C. 154(b) by 77 days.

(21) Appl. No.: 17/385,378

(22) Filed: Jul. 26, 2021

(65) Prior Publication Data

US 2021/0349031 A1 Nov. 11, 2021

Related U.S. Application Data

(63) Continuation of application No. 16/419,952, filed on May 22, 2019, now Pat. No. 11,073,481, which is a continuation of application No. 15/845,754, filed on Dec. 18, 2017, now Pat. No. 10,324,041.

(60) Provisional application No. 62/437,534, filed on Dec. 21, 2016.

(51) Int. Cl.
*G01N 21/64* (2006.01)
*G01N 33/543* (2006.01)
*G01N 21/51* (2006.01)
*G01N 21/75* (2006.01)

(52) U.S. Cl.
CPC ............. *G01N 21/75* (2013.01); *G01N 21/51* (2013.01); *G01N 21/64* (2013.01); *G01N 21/645* (2013.01); *G01N 21/6428* (2013.01); *G01N 21/6452* (2013.01); *G01N 33/54366* (2013.01);
(Continued)

(58) Field of Classification Search
CPC .... G01N 21/51; G01N 21/64; G01N 21/6428; G01N 21/645; G01N 21/6452; G01N 21/75; G01N 33/54366; G01N 2201/0621; G01N 2201/063
See application file for complete search history.

(56) References Cited

U.S. PATENT DOCUMENTS

| 5,026,159 A | 6/1991 | Allen et al. |
| 5,162,990 A | 11/1992 | Odeyale et al. |
| 5,260,578 A | 11/1993 | Bliton et al. |

(Continued)

FOREIGN PATENT DOCUMENTS

| JP | 3727026 | 12/2005 |
| WO | WO 2001058956 | 8/2001 |

(Continued)

OTHER PUBLICATIONS

Banta et al., "Replacing antibodies: engineering new binding proteins." Annu Rev Biomed Eng. 2013; 15:93-113.
(Continued)

*Primary Examiner* — Mark R Gaworecki
(74) *Attorney, Agent, or Firm* — Casimir Jones SC; Lisa Mueller

(57) ABSTRACT

A compact optical imaging system including a single filter and a light source that provides lateral illumination for bead detection in digital assays. The light source is configured to emit light toward the detection vessel. The single filter is positioned to receive light reflected from a sample in the detection vessel, that originated from the light source, and receive an output from a sample in the detection vessel. A detector is configured to receive a portion of the reflected light and a portion of the output that passes through the single filter.

14 Claims, 12 Drawing Sheets

(52) U.S. Cl.
CPC ............... *G01N 2201/063* (2013.01); *G01N 2201/0621* (2013.01)

(56) References Cited

U.S. PATENT DOCUMENTS

| | | | |
|---|---|---|---|
| 5,481,401 | A | 1/1996 | Kita et al. |
| 5,620,850 | A | 4/1997 | Bamdad et al. |
| 5,811,312 | A | 9/1998 | Hasegawa et al. |
| 5,880,473 | A | 3/1999 | Ginestet |
| 6,169,816 | B1 | 1/2001 | Ravkin |
| 6,259,807 | B1 | 7/2001 | Ravkin |
| 6,266,459 | B1 | 7/2001 | Walt et al. |
| 6,385,272 | B1 | 5/2002 | Takahashi |
| 7,050,613 | B2 | 5/2006 | Murao et al. |
| 7,070,921 | B2 | 7/2006 | Huang et al. |
| 7,272,252 | B2 | 9/2007 | De La Torre-Bueno et al. |
| 7,602,952 | B2 | 10/2009 | Kersey et al. |
| 7,838,250 | B1 | 11/2010 | Goix et al. |
| 7,843,634 | B2 | 11/2010 | Kawahito |
| 8,031,918 | B2 | 10/2011 | Roth |
| 8,304,026 | B2 | 11/2012 | Smith et al. |
| 8,460,879 | B2 | 6/2013 | Walt et al. |
| 8,704,196 | B2 | 4/2014 | Wolleschensky et al. |
| 8,759,790 | B2 | 6/2014 | Kishima et al. |
| 8,791,427 | B2 | 7/2014 | Honda et al. |
| 8,912,007 | B2 | 12/2014 | Bjornson et al. |
| 9,110,306 | B2 | 8/2015 | Hayashi et al. |
| 9,224,031 | B2 | 12/2015 | Glensbjerg et al. |
| 9,310,302 | B2 | 4/2016 | Garsha et al. |
| 2002/0177751 | A1 | 11/2002 | Ueno et al. |
| 2003/0096302 | A1 | 5/2003 | Yguerabide |
| 2003/0151735 | A1 | 8/2003 | Blumenfeld et al. |
| 2005/0083536 | A1 | 4/2005 | Fouquet |
| 2005/0118584 | A1 | 6/2005 | Nomura |
| 2006/0121544 | A1 | 6/2006 | Boge et al. |
| 2006/0154303 | A1 | 7/2006 | Myogadani |
| 2007/0141645 | A1 | 6/2007 | Okamura et al. |
| 2007/0263210 | A1 | 11/2007 | Taguchi et al. |
| 2008/0032324 | A1 | 2/2008 | Walt et al. |
| 2008/0240543 | A1 | 10/2008 | Budach et al. |
| 2008/0254492 | A1 | 10/2008 | Tsuchiya et al. |
| 2009/0015831 | A1 | 1/2009 | Yguerabide |
| 2009/0021735 | A1 | 1/2009 | Shigeura |
| 2009/0315987 | A1 | 12/2009 | Straus |
| 2010/0228513 | A1 | 9/2010 | Roth et al. |
| 2011/0195852 | A1 | 8/2011 | Walt et al. |
| 2011/0236964 | A1 | 9/2011 | Oldham |
| 2012/0140055 | A1 | 6/2012 | Narusawa et al. |
| 2012/0196296 | A1 | 8/2012 | Oldham |
| 2012/0196774 | A1 | 8/2012 | Fournier et al. |
| 2012/0212740 | A1 | 8/2012 | Oldham |
| 2012/0274760 | A1 | 11/2012 | King et al. |
| 2013/0011842 | A1 | 1/2013 | Oldham |
| 2014/0206580 | A1 | 7/2014 | Grudzien et al. |
| 2014/0323330 | A1 | 10/2014 | Bergo |
| 2015/0060700 | A1 | 3/2015 | Bjornson et al. |
| 2015/0070699 | A1 | 3/2015 | King et al. |
| 2015/0185152 | A1 | 7/2015 | Maher |
| 2015/0247190 | A1 | 9/2015 | Ismagilov et al. |
| 2015/0308944 | A1 | 10/2015 | Bjornson et al. |
| 2015/0355079 | A1 | 12/2015 | Empedocles et al. |
| 2015/0355182 | A1 | 12/2015 | Rissin et al. |
| 2016/0041094 | A1 | 2/2016 | Lei |
| 2016/0217315 | A1 | 7/2016 | Adalsteinsson et al. |
| 2016/0228876 | A1 | 8/2016 | Chu et al. |
| 2016/0230210 | A1 | 8/2016 | Chen et al. |
| 2016/0245805 | A1 | 8/2016 | Baer et al. |
| 2016/0333400 | A1 | 11/2016 | Makino et al. |
| 2017/0023566 | A1 | 1/2017 | Merandon et al. |
| 2017/0343466 | A1 | 11/2017 | Dou et al. |
| 2017/0343476 | A1 | 11/2017 | Boege |
| 2018/0023124 | A1 | 1/2018 | Collins et al. |

FOREIGN PATENT DOCUMENTS

| | | |
|---|---|---|
| WO | WO 2007104057 A2 | 9/2007 |
| WO | WO 2012121310 | 9/2012 |
| WO | WO 2016006208 | 1/2016 |

OTHER PUBLICATIONS

Behar et al., "Tolerance of the archaeal Sac7d scaffold protein to alternative library designs: characterization of anti-immunoglobulin G Affitins." Protein Eng Des Sel. Apr. 2013;26(4):267-75.

Chang et al., "Single molecule enzyme-linked immunosorbent assays: Theoretical considerations." Journal of Immunological Methods 378 (2012), 102-115.

Esparza et al., "Amyloid-Beta Oligomerization in Alzheimer Dementia versus High-Pathology Controls." American Neurological Association 2012, 73:104-107.

Gilbreth & Koide, "Structural insights for engineering binding proteins based on non-antibody scaffolds." Curr Opin Struct Biol. Aug. 2012;22(4):413-20.

Gottlin et al., "Isolation of novel EGFR-SPEC; IDS Jun. 25, 2018 ific VHH domains." J Biomol Screen. Jan. 2009; 14(1):77-85.

Heller, "Electrical wiring of redox enzymes," Acc. Chem. Res., 1990, 23(5):128-134.

Holt et al., "Domain antibodies: proteins for therapy" Trends in Biotechnology, 2014, 21:484-490.

Jeromin, "Ultrasensitive Detection of Neurodegenerative Biomarkers in Blood With The Fully automated Simoa Analyzer: Clinical Applications." Poster Presentations: P515-516. 2014.

Jetha et al., "Nanopore Analysis of Wild-Type and Mutant Prion Protein (PrPC): Single Molecule Discrimination and PrPC Kinetics." Plos One Feb. 2013, 8(2):e54982.

Kan et al., "Isolation and detection of single molecules on paramagnetic beads using sequential fluid flows in microfabricated polymer array assemblies." Lab Chip, 2012, 12:977-985.

Kim et al., "Large-scale femtoliter droplet array for digital counting of single biomolecules." Lab Chip. Dec. 7, 2012; 12(23):4986-91.

Kuhle, "Comparison of three analytical platforms for quantification of the neurofilament light chain in blood samples: ELISA, electrochemiluminescence immunoassay and Simoa." Clin Chem Lab Med 2016; 54(10): 1655-1661.

Lepor et al., "Clinical evaluation of a novel method for the measurement of prostate-SPEC; IDS Jun. 25, 2018 ifi c antigen, AccuPSA TM, as a predictor of 5-year biochemical recurrence-free survival after radical prostatectomy: results of a pilot study." BJU International 2011, 109:1770-1775.

McEnaney et al., "Antibody-recruiting molecules: an emerging paradigm for engaging immune function in treating human disease." ACS Chem Biol. Jul. 20, 2012; 7(7):1139-51.

Merouane et al., "Automated profiling of individual cell-cell interactions from high-throughput time-lapse imaging microscopy in nanowell grids (TIMING)." Bioinformatics. Oct. 1, 2015; 31(19):3189-97.

Millward et al., "Iterative in situ click chemistry assembles a branched capture agent and allosteric inhibitor for Akt1." J Am Chem Soc. Nov. 16, 2011; 133(45):18280-8.

Neuweiler et al., "Sensitive detection of p53 antibodies in a homogenous fluorescence assay format." Biomedical Nanotechnology Architectures and Applications, Darryl J. Bornhop, et al., Editors, Proceedings of SPIE vol. 4626 (2002), 259-267.

Obayashi et al., "A single-molecule digital enzyme assay using alkaline phosphatase with a cumarin-based fluorogenic substrate." Analyst 2015, 140: 5065-5073.

Patel et al. "Selection of a high-affinity WW domain against the extracellular region of VEGF receptor isoform-2 from a combinatorial library using CIS display." Protein Eng Des Sel. Apr. 2013; 26(4):307-15.

Radar, "Chemically programmed antibodies." Trends in Biotechnology, 2014, 32:186-197.

Rissin et al., "Simultaneous Detection of Single Molecules and Singulated Ensembles of Molecules Enables Immunoassays with Broad Dynamic Range." Analytical Chemistry, 2011, 83:2279-2285.

(56) References Cited

OTHER PUBLICATIONS

Rissin et al., "Single-molecule enzyme-linked immunosorbent assay detects serum proteins at subfemtomolar concentrations." Nature Biotechnology Jun. 2010, 28(6):595-599.
Rondelez et al., "Microfabricated arrays of femtoliter chambers allow single molecule enzymology." Nat Biotechnol. Mar. 2005; 23(3):361-5.
Schubert et al., "Ultra-sensitive protein detection via Single Molecule Arrays towards early stage cancer monitoring." Jun. 8, 2015, 5:11034.
Shim et al., "Ultrarapid Generation of Femtoliter Microfluidic Droplets for Single-Molecule-Counting Immunoassays." ACSNANO 2013, 7(7):5955-5964.
Tessler et al., "Sensitive single-molecule protein quantification and protein complex detection in a microarray format." Proteomics 2011, 11:4731-4735.
Tiede et al., "Adhiron: a stable and versatile peptide display scaffold for molecular recognition applications." Protein Eng Des Sel. May 2014; 27(5):145-55.
Wu et al., "Simultaneous targeting of multiple disease mediators by a dual-variable-domain immunoglobulin." Nat Biotechnol. Nov. 2007;25(11):1290-7.
Xu et al., "Novel solution-phase immunoassays for molecular analysis of tumor markers." Analyst 2001, 126: 1285-1292.
Zetterberg et al., "Hypoxia Due to Cardiac Arrest Induces a Time-Dependent Increase in Serum Amyloid b Levels in Humans." PLoS ONE Dec. 20, 2011, 6(12):e28263.
Extended European Search Report for European Application No. 17882684.8 dated Jul. 2, 2020.
National Intellectual Property Administration, P.R. China, First Office Action for Chinese Application No. 201780087035.5, dated Aug. 30, 2021.

| Conventional | Specifications | Compact |
|---|---|---|
| Fluorescence/Fluorescence | Imaging System: dual channel (for bead/enzyme) | Light-scattering/Fluorescence |
| ~70x50x50 | Size / cm | ~12x10x10, handheld |
| 30,000 | Imaging area / chamber-area | 100,000 |
| In a dark room | Image Acquisition | Under ambient conditions |
| AC100V | Power | Lines (USB, 100mA and 2A) |
| Tower PC | Processor | Mini PC, 5inch (CPU/RAM: Intel ATOM/2GB) |

OPTICAL IMAGING SYSTEM USING LATERAL ILLUMINATION FOR DIGITAL ASSAYS

CROSS-REFERENCE TO RELATED APPLICATIONS

This application is a continuation of copending U.S. application Ser. No. 16/419,952, filed May 22, 2019, which is a continuation of U.S. application Ser. No. 15/845,754, filed Dec. 18, 2017, now U.S. Pat. No. 10,324,041 which claims benefit of U.S. Provisional Patent Application No. 62/437,534, filed on Dec. 21, 2016, the entire contents of which are incorporated herein by reference.

TECHNICAL FIELD

This disclosure relates to an optical imaging system including a single filter and a light source that provides lateral illumination for analyte analysis in digital assays.

BACKGROUND OF THE INVENTION

Devices and methods that can accurately analyze analyte(s) of interest in a sample are essential for diagnostics, such as for example diagnosing a disease, disorder or condition, prognostics, environmental assessment, food safety, detection of chemical or biological warfare agents and the like. Most current techniques for quantifying low levels of analyte molecules in a sample use amplification procedures to increase the number of reporter molecules to provide a measurable signal. Examples of current techniques include enzyme-linked immunosorbent assays (ELISA) for amplifying the signal in antibody-based assays, as well as the polymerase chain reaction (PCR) for amplifying target DNA strands in DNA-based assays. Most detection schemes require the presence of a large number of molecules in the ensemble for the aggregate signal to be above the detection threshold. This requirement limits the sensitivity of most detection techniques and the dynamic range (i.e., the range of concentrations that can be detected). Many of the known methods and techniques are further plagued with problems of non-specific binding, which leads to an increase in the background signal and limits the lowest concentration that may be accurately or reproducibly detected.

Digital ELISA is a candidate for next generation of immunoassay as it can detect one molecule of enzyme using a conjugate. See FIGS. 1 and 2. In digital ELISA, target molecules are captured on beads between a capture antibody and a detection antibody, wherein the detection antibody is bound to an enzyme. The beads are then entrapped in a droplet chamber with the substrate of the enzyme, and the aqueous phase is displaced by a heavy oil, allowing removal of the aqueous phase before analysis.

In bead-based digital ELISA, single beads are encapsulated in microchambers of the array. Some of the chambers in which a bead has captured an immune-complex species provide bright spots upon fluorescence imaging (i.e., a bright chamber). The percentage of chambers having beads present is correlated to concentration of antigen. Therefore, it is necessary to identify positions of beads and enzymes in the microchambers of the array.

Optical imaging is a method to determine the location of beads in an assay. Optical imaging can also detect data for a large number (over 10,000) of microchambers at a time using bead/enzyme dual channel imaging. However, conventional optical systems for dual channel imaging are large and expensive to mount on existing products because of the complicated optics for fluorescence/fluorescence type of bead/enzyme dual channel imaging. Conventional optical systems require multiple optical filters for the respective channels, and an external actuator for exchanging the modes.

SUMMARY OF THE INVENTION

Accordingly, it is desirable to provide a simplified optical imaging system for digital immunoassay that provides for a compact and low cost digital immunoassay device. Embodiments of the invention provide an imaging system using light scattering optics for digital immunoassay where size and cost are substantially reduced compared to a conventional optical imaging system.

Embodiments of the invention simplify the optical imaging system by employing a light source that applies light scattering to the assay for bead detection. The optical imaging system utilizes light-scattering/fluorescence type and has been simplified by removing optical components and the corresponding actuator structure for the mode exchange used in a conventional system. To demonstrate the power of the optical imaging system according to embodiments of the system, a compact device for digital ELISA was designed and tested. The embodiments of the optical imaging system demonstrated good performance and were comparable or superior to a conventional optical imaging system. (Noteworthy specifications are summarized in FIG. 1.) The detector is approximately several 10s and 100 times smaller in volume and cost, respectively.

In one embodiment, the invention provides a compact digital assay apparatus comprising a detection vessel, a light source configured to emit light toward the detection vessel, a single filter and a detector. The single filter is positioned to receive light reflected from a sample in the detection vessel, that originated from the light source, and receive an output from a sample in the detection vessel. The detector is configured to receive a portion of the reflected light and a portion of the output that passes through the single filter.

In another embodiment, the invention provides a compact digital assay apparatus comprising a detection vessel, a first light source configured to emit light toward the detection vessel and at an angle relative to the sample array, a second light source configured to emit light toward the detection vessel, a single filter, and a detector. The single filter is positioned to receive light reflected from a sample in the detection vessel, that originated from the first light source, and receive a fluorescence output from a sample in the detection vessel. The detector is configured to receive a portion of the reflected light and a portion of the fluorescence that passes through the single filter.

In a further embodiment, the invention provides a compact digital assay apparatus comprising a sample array having a plurality of wells, a first light source configured to emit light toward the sample array at an angle relative to the sample array to illuminate a sample in the sample array, a second light source configured to emit light toward the sample array without using a mirror or other reflective object, the second light source further configured to activate a sample in the sample array to emit an output, a filter, and a detector. The filter is positioned to receive light reflected from the sample array that originated from the first light source, and receive the output from the sample in the sample array. The detector is configured to receive the reflected light and the output from the sample that pass through the filter and to generate optical data identifying which wells contain a bead and which wells contain a label.

In yet another embodiment, the invention provides a compact digital assay apparatus comprising a sample array including a plurality of samples positioned in a plurality of nanowells, a light source configured to emit light toward the sample array at an angle relative to the sample array to illuminate a sample in the sample array, the light source having a wavelength between 450 nm and 550 nm, and a detector configured to receive a portion of light reflected from the sample.

Other aspects of the invention will become apparent by consideration of the detailed description and accompanying drawings.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

1. Definitions

Figure 1:
FIG. 1 is a comparison of a simplified optical imaging system according to an embodiment of the present invention and a conventional optical imaging system.
Figure 2:
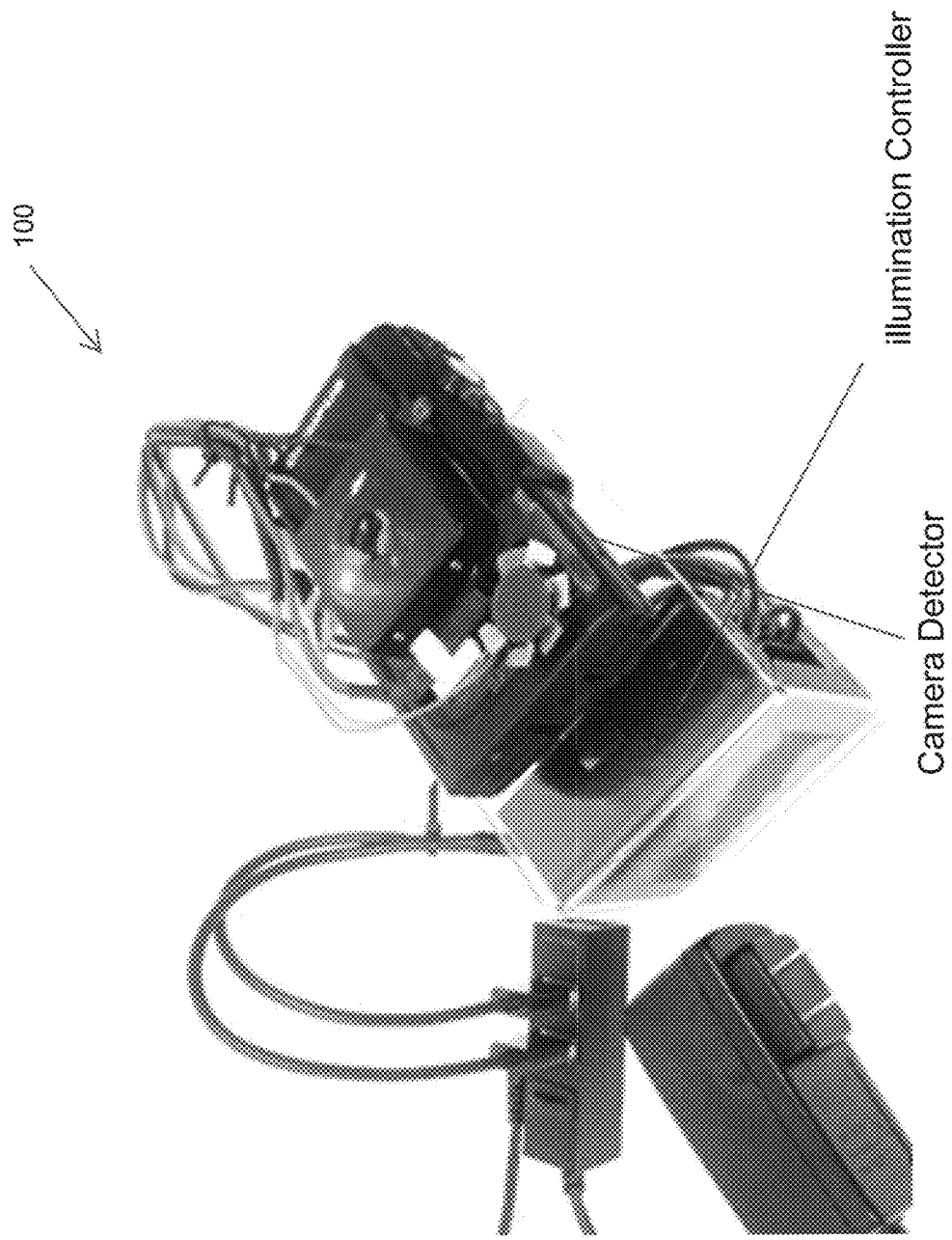
FIG. 2 is a perspective view of an optical imaging system according to an embodiment of the present invention.
Figure 3:
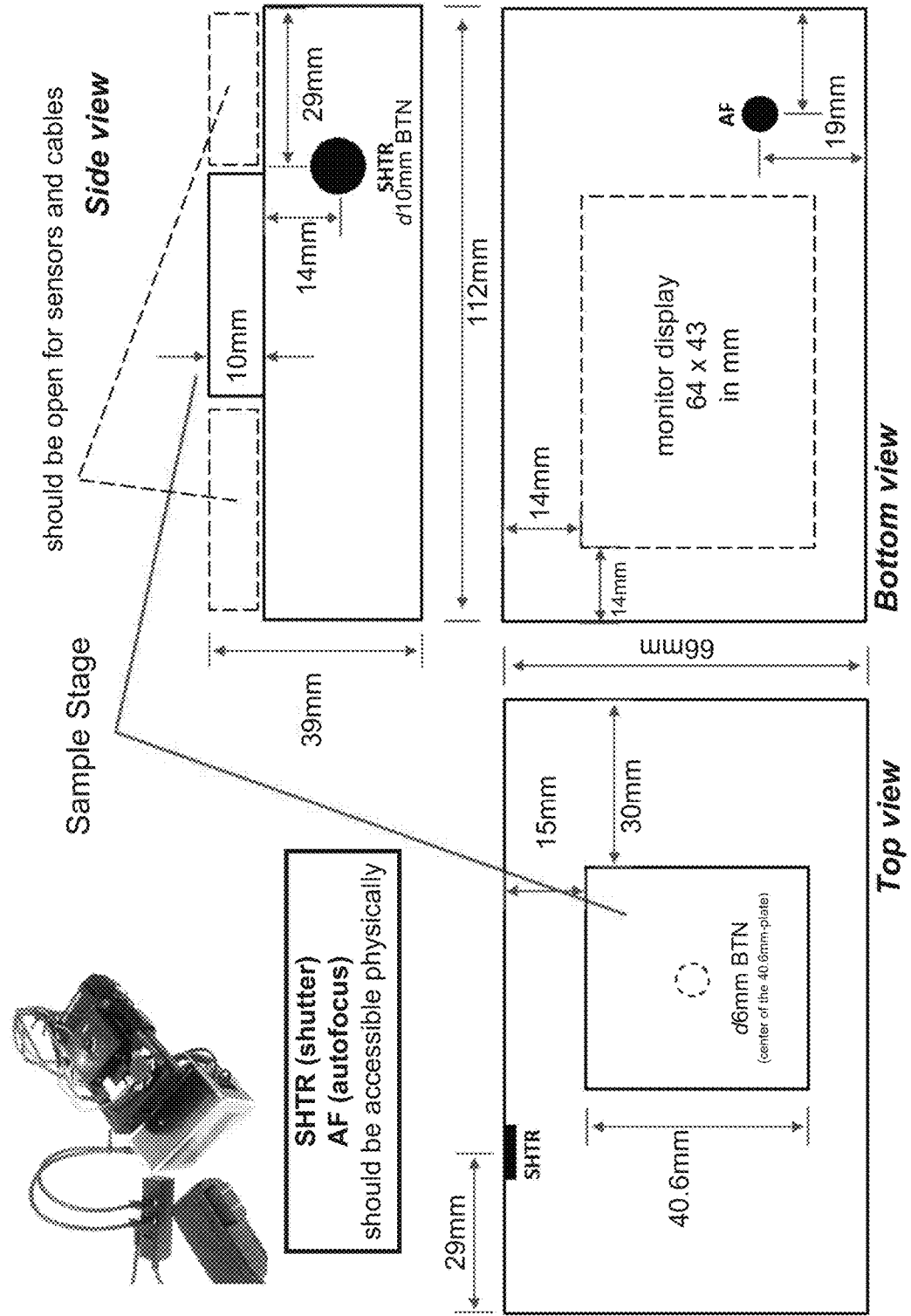
FIG. 3 shows several views of the optical imaging system illustrated in FIG. 2.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity" and "binding affinity" as used interchangeably herein refer to the tendency or strength of binding of the binding member to the analyte. For example, the binding affinity may be represented by the equilibrium dissociation constant (KD), the dissociation rate (kd), or the association rate (ka).

"Analog" as used herein refers to a molecule that has a similar structure to a molecule of interest (e.g., nucleoside analog, nucleotide analog, sugar phosphate analog, analyte analog, etc.). An analyte analog is a molecule that is structurally similar to an analyte but for which the binding member has a different affinity.

"Analyte", "target analyte", "analyte of interest" as used interchangeably herein, refer to an analyte being measured in the methods and devices disclosed herein. Analytes of interest are further described herein.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Patent Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody."

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Bead" and "particle" are used herein interchangeably and refer to a substantially spherical solid support.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Capture molecule" as used herein refers to a specific binding partner or specific binding member used to capture or immobilize an analyte of interest in a biological sample. A capture molecule is often one component of a complex in addition to the analyte of interest and may also contain one or more detection molecules. The complex may optionally be bound to a solid support.

"Component," "components," or "at least one component," refer generally to a capture antibody, a detection reagent or conjugate, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as patient urine, serum, whole blood, tissue aspirate, or plasma sample, in accordance with the methods described herein and other methods known in the art. Some components can be in solution or lyophilized for reconstitution for use in an assay.

"Contacting" and grammatical equivalents thereof as used herein refer to any type of combining action which brings a binding member into sufficiently close proximity with the analyte of interest in the sample such that a binding interaction will occur if the analyte of interest specific for the binding member is present in the sample. Contacting may be achieved in a variety of different ways, including combining the sample with a binding member, exposing a target analyte to a binding member by introducing the binding member in close proximity to the analyte, and the like.

"Control" as used herein refers to a reference standard for an analyte such as is known or accepted in the art, or determined empirically using acceptable means such as are commonly employed. A "reference standard" is a standardized substance which is used as a measurement base for a similar substance. For example, there are documented reference standards published in the U.S. Pharmacopeial Convention (USP-NF), Food Chemicals Codex, and Dietary Supplements Compendium (all of which are available at http://www.usp.org), and other well-known sources. Methods for standardizing references are described in the literature. Also well-known are means for quantifying the amounts of analyte present by use of a calibration curve for analyte or by comparison to an alternate reference standard. A standard curve can be generated using serial dilutions or solutions of known concentrations of analyte, by mass spectroscopy, gravimetric methods, and by other techniques known in the art. Alternate reference standards that have been described in the literature include standard addition (also known as the method of standard addition), or digital polymerase chain reaction.

"Detection molecule" as used herein refers to a specific binding partner or specific binding member that is used to detect the presence of and/or quantify or measure the amount of an analyte of interest in a biological sample. A detection molecule is often one component of a complex that may contain a one or more capture molecules and an analyte of interest. The complex may optionally be bound to a solid support.

"Detection" or "reaction" vessel as used herein refers a container or other apparatus that may contain a reaction mixture that may or may not contain an analyte of interest. Examples of suitable "detection" or "reaction" vessels include a cuvette, a tube, the individual tube(s) of the tube plate, the hole(s) or well(s) in the microliter plate, the individual reaction well(s) (such as an array of wells such as a microwell array or a nanowell array) or pit(s) in the test slide plate or assay array plate.

"Immobilized" as used herein, refers to a stable association of the first specific binding member with a surface of a solid support. By "stable association" is meant a physical association between two entities in which the mean half-life of association is one day or more, e.g., under physiological conditions. In certain aspects, the physical association between the two entities has a mean half-life of two days or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Other labels are described herein. In this regard, the moiety, itself, may not be detectable but may become detectable upon reaction with yet another moiety. Use of the term "detectably labeled" is intended to encompass such labeling.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Polynucleotides" or "oligonucleotides" refer to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof. "Nucleic acid" encompasses "polynucleotide" and "oligonucleotides" and includes single stranded and double stranded polymers of nucleotide monomers.

"Predetermined cutoff" and "predetermined level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

"Receptor" as used herein refers to a protein-molecule that recognizes and responds to endogenous-chemical signals. When such endogenous-chemical signals bind to a receptor, they cause some form of cellular/tissue-response. Examples of receptors include, but are not limited to, neural receptors, hormonal receptors, nutrient receptors, and cell surface receptors.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Sample," "test sample," "biological sample," "sample from a subject," "fluid biological sample," and "patient sample" as used herein may be used interchangeable and refer to fluid sample containing or suspected of containing an analyte of interest.

As used herein "sample array" refers to a collection of one or more (or a plurality of) detection or reaction vessels.

As used herein, "signal generating compound" refers to any molecule, compound, protein or the like that can be converted to a detectable product or detectable label upon exposure to a suitable or appropriate converting agent, such as a signal generating substrate. A "detectable product" or "detectable label" is any molecule, particle, or the like, that facilitates detection, by acting as the detected entity, using a chosen technique known in the art. An example of a signal generating compound is an enzyme such as amylases, polynucleotidase, arginase, adenase, aminopolypeptidase, pepsin, lipases, catalase, tyrosinases, alcohol dehydrogenase, succinic dehydrogenase, diaphorase, glyoxalase, aldolase, glucose oxidase, horseradish peroxidase, a galactosidase (such as beta-galactosidase), phosphatases, phosphorylases and hexokinases or combinations thereof.

As used herein "signal generating substrate" refers any molecule, compound, protein, substance, particle, or the like, that can be converted to or result in a signal generating compound being converted to a detectable product or detectable label upon exposure to a suitable or appropriate converting agent, such as a signal generating compound. A "detectable compound" or "detectable label" is any molecule, particle, or the like, that facilitates detection, by acting as the detected entity, using a chosen technique known in the art. Signal generating substrates can be colorimetric, chemiluminescent or chemifluorescent. An example of a signal generating substrate is an enzymatic substrate, such as a chemiluminescent substrate such as CDP-Star®, (disodium 4-chloro-3-(methoxyspiro{1,2-dioxetane-3,2'-(5'-chloro)tricyclo[3.3.1.1.s-up.3,7]decane}-4-yl)phenyl phosphate), CSPD®, or (disodium 3-(4-methoxyspiro{1,2-dioxetane-3, 2-(5'-chloro)tricyclo[3.3.1.1-.sup.3,7]decane}-4-yl)phenyl phosphate); a luminescent substrate such as p-nitrophenyl phosphate, 5-bromo-4-chloro-3-indolyl phosphate (BCIP), 4-nitro blue tetrazolium chloride (NBT), or iodonitrotetrazolium (INT); a fluorescent substrate such as 4-methylumbelliferyl phosphate (4-MUP); and a chromogenic substrate such as 5-bromo-4-chloro-3-indolyl phosphate (BCIP), disodium 5-bromo-6-chloro-indolyl phosphate, or p-nitrophenyl phosphate.

"Specific binding partner" or "specific binding member" as used interchangeably herein refers to one of two or more different molecules that specifically recognize the other molecule compared to substantially less recognition of other molecules. The one of two different molecules has an area on the surface or in a cavity, which specifically binds to and is thereby defined as complementary with a particular spatial and polar organization of the other molecule. The molecules may be members of a specific binding pair. For example, a specific binding member may include, but is not limited to, a protein, such as a receptor, an enzyme, and an antibody.

In addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Solid support" refers to any material that is insoluble, or can be made insoluble by a subsequent reaction. The solid support can be chosen for its intrinsic ability to attract and immobilize a capture agent. Alternatively, the solid support can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid support and that has the ability to immobilize the capture agent through a binding reaction. The linking agent enables the indirect binding of the capture agent to a solid support material before the performance of the assay or during the performance of the assay. For examples, the solid support can be plastic, derivatized plastic, magnetic, or non-magnetic metal, glass or silicon, including, for example, a test tube, microtiter well, sheet, bead, microparticle, chip, and other configurations known to those of ordinary skill in the art.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Threshold" as used herein refers to an empirically determined subjective cutoff level above which acquired data is considered "signal," and below which acquired data is considered "noise." A computer program based on CUSUM (Cumulative Sums Algorithm) is employed to process acquired data and detect events based on threshold input from the user. Variation between users is avoided by detection of any many events as possible followed by filtering the data afterwards for specific purposes. With a "loose" threshold a lesser number of events will be counted as signal. With a "tight" threshold a greater number of events will be counted as signal. Setting the threshold as loose or tight is a subjective choice based on the desired sensitivity or specificity for an assay, and whether in a given assessment false positives or false negatives would be preferred.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety to disclose and describe the methods and/or materials in connection with which the publications are cited. The materials, methods, and examples disclosed herein are illustrative only and not intended to be limiting.

1. OPTICAL IMAGING SYSTEM

The present invention provides a compact and relatively low cost apparatus for conducting a digital assay, such as a digital immunoassay, to detect and/or quantify an analyte of interest in a sample. The apparatus may be handheld or positioned on a support surface or connected to and supported by adjacent processing equipment. The apparatus described herein provides a number of benefits over conventional optical imaging systems known in the art. For example, the apparatus of the present disclosure is compact, provides a larger imaging area, and includes a simplified structure, etc. As noted in FIG. 1, an embodiment of the present invention is compared to a conventional system (e.g., an optical microscope system). The size of the apparatus of the present invention is significantly smaller than a conventional system. For example, one construction of the apparatus measures 12 cm×10 cm×10 cm while the conventional system measures 70 cm×50 cm×50 cm. In this construction, the apparatus is about 5 times smaller than the conventional system. Additionally, the imaging area of the apparatus of the present invention is 100,000 sample chambers, which measures about 30 mm$^2$, compared to 30,000 sample chambers, which measures about 9 mm², for a conventional system. Image acquisition can occur under ambient conditions for embodiments of the present invention while the conventional system requires a dark room. Additional comparisons between embodiments of the present invention and a conventional system are shown in FIG. 1.

The construction of the apparatus of the present invention also is less complicated than the construction of the conventional system. The conventional system, which utilizes fluorescence imaging techniques for detection of one or more analytes of interest in a sample, requires multiple optical filters for each of the two channels along with actuators for exchanging the filters. The present apparatus utilizes a light scattering imaging technique for analyte detection and a light source oriented at an angle relative to the sample array (comprising one or more detection or reaction vessels) thus allowing use of a single filter and elimination of the multiple filters and the actuators that are used in the conventional system. Additionally, the color of the light source can be selected based on the emission filter that is used for analyte detection, thereby allowing use of a single filter for analyte detection.

According to an embodiment, the apparatus comprises a number of components, including one or more detection or reaction vessels, a light source configured to emit light toward the detection vessel, a single filter positioned to receive light reflected from a sample in the one or more detection vessels, that originated from the light source, and receive an output from a sample in the detection vessel, and a detector configured to receive a portion of the reflected light and a portion of the output that passes through the single filter.

Figure 4:
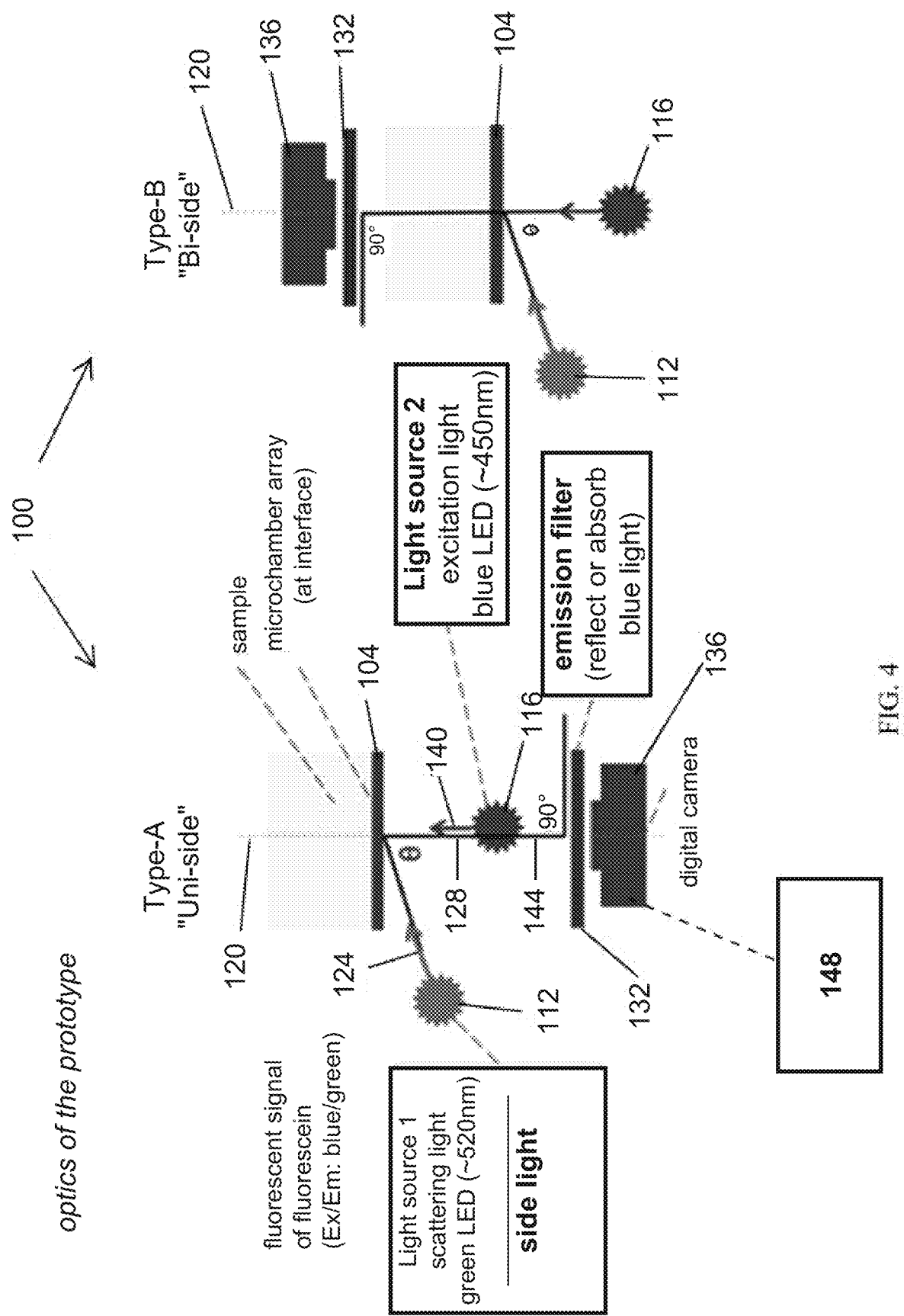
FIG. 4 is a schematic of an optical imaging system according to an embodiment of the present invention.

FIGS. 2-5 illustrate an optical imaging system 100 according to an embodiment of the present invention. With reference to FIG. 4, the optical imaging system 100 is configured to detect solid supports (such as beads) that may contain an analyte of interest in a detection vessel 104 (such as a sample array comprising a plurality of microwells or nanowells) and to detect an output from the sample in the detection vessel 104 upon activation of the sample (such as by using a detectable label).

The optical imaging system 100 may include a support 108 for receiving the detection vessel 104. The system 100 also includes a first light source 112 and may include a second light source 116. The first light source 112 may be comprised of a single light source or a plurality of light sources. The first light source 112 is positioned above or below the detection vessel 104 and is oriented at an angle θ relative to an axis 120 extending generally perpendicular to the detection vessel 104. For example, generally perpendicular includes 90 degrees+/−about 2 degrees (i.e., 88 degrees to 92 degrees) relative to the detection vessel 104. The angle θ is between about 0 degrees and about 90 degrees. In other embodiments, the angle θ is between about 45 degrees and about 90 degrees. In another embodiment, the angle θ is 80 degrees.

The first light source 112 emits scattered light 124 toward the detection vessel 104. The first light source 112 can comprise a light-emitting diode (LED) that emits light at a particular wavelength. For example, the first light source 112 can comprise a green LED that emits light at about 520 nm. The scattered light 124 reflects off the sample in the detection vessel 104 as reflected light 128, which is received by a filter 132. The filter 132 allows a portion of the reflected light 128 through to a detector or camera 136. The camera 136 generates an image, which presents bright pixels that visualize or determine positions of any solid supports (e.g., beads) containing the analyte of interest in the image. The image(s) aids in the determination of the number of detection vessels which contain a solid support containing an analyte of interest and/or provide spatial information regarding the position of the locations. See, for example, FIG. 6, which illustrates images (A) and (D) generated with a first light source 112 as described above. In other constructions, the color of the LED of the first light source 112 can be selected based on the filter 132 used in the apparatus.

Figure 5:
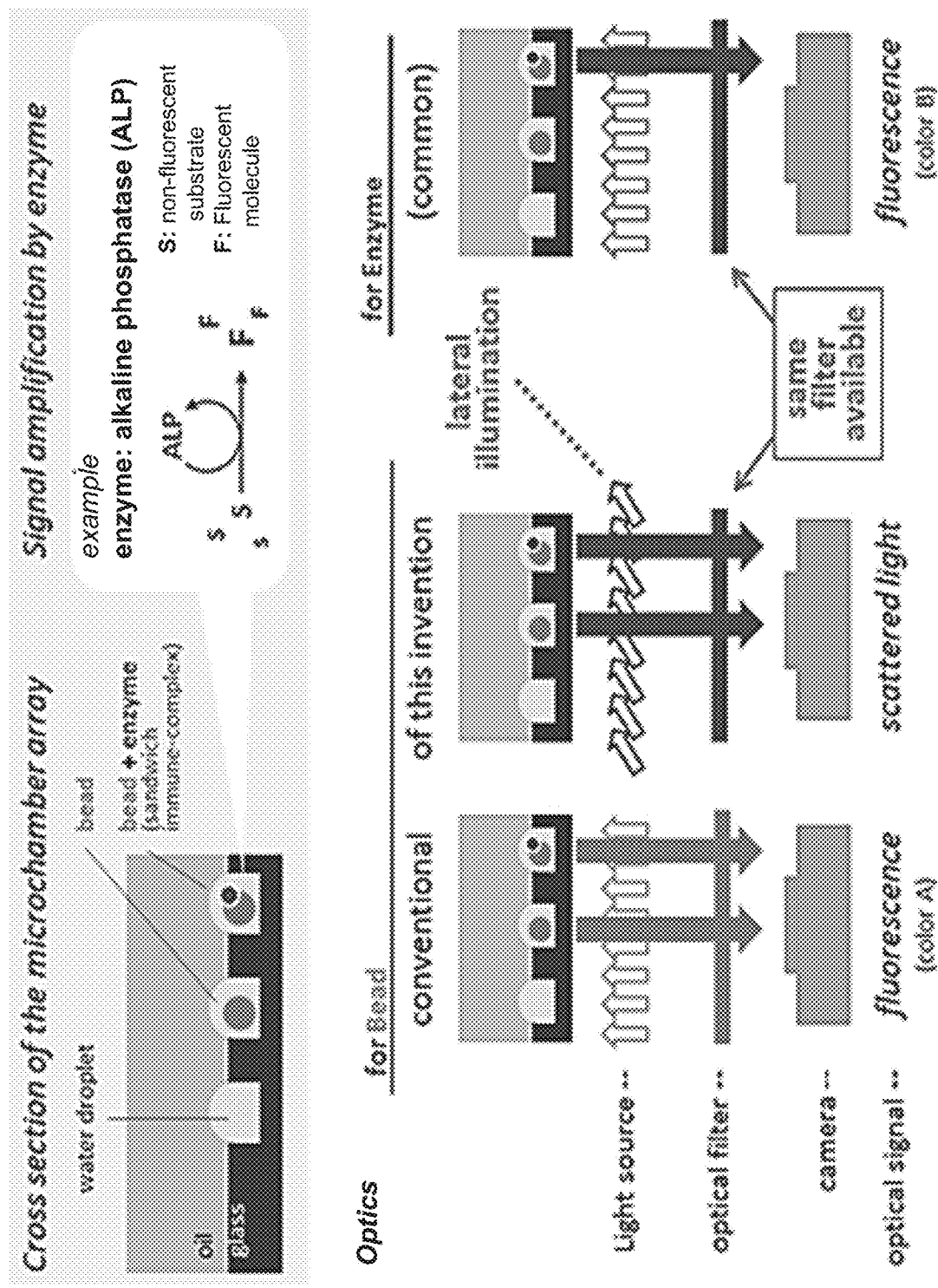
FIG. 5 schematic illustration of a microchamber array for digital immunoassay and a mechanism of fluorescent signal amplification by an enzymatic reaction (top images); comparison of differences between optical imaging system of a convention system and the optical imaging system illustrated in FIG. 2.

With continued reference to FIGS. 4 and 5, the second light source 116 is positioned above or below the detection vessel 104 and is oriented generally perpendicular relative to the detection vessel 104. For example, generally perpendicular includes 90 degrees and + or − about 2 degrees (i.e., 88 degrees to 92 degrees relative to the detection vessel 104). In some embodiments, the second light source 116 is positioned along the axis 120, while in other embodiments, the second light source 116 is positioned adjacent to the axis 120. For example, as illustrated in FIG. 4 (Type A), the second light source 116 is laterally offset from the axis 120 so as to not disturb the scattered light reflected from the samples and fluorescence emitted from samples (discussed below).

The second light source 116 emits excitation light 140 toward the detection vessel 104. The second light source 116 can comprise a LED that emits excitation light at a particular wavelength. For example, the second light source 116 can comprise a blue LED that emits light at about 450 nm. The excitation light 140 excites or activates the samples in the detection vessel 104. For example, if a particular analyte is present in the sample(s), then the sample(s) emits an output 144, such as a fluorescence. If the particular analyte is not present in the sample(s) then an output 144 is not produced. The filter 132 (same as the filter that receives the reflected light 128) receives the output 144 and allows the output 144 through to the camera 136. The camera 136 generates an image, which presents bright pixels that visualize or determine which detection vessels contain the particular analyte of interest. See, for example, FIG. 6, which illustrates images (B) and (E) generated with a second light source 116 as described above. The second light source 116 can be specifically selected (e.g., LED color) based on the filter 132 that is employed for analyte detection in the samples.

The camera 136 can be a CCD camera used to capture images. Other examples of cameras include charge injection devices (CIDs), complementary metal oxide semiconductor (CMOS) devices, scientific CMOS (sCMOS) devices, and time delay integration (TDI) devices.

The camera 136 can be electronically or communicatively coupled to a computer 148. The computer 148 includes an electronic processor (for example, a microprocessor, application-specific integrated circuit (ASIC), or another suitable electronic device), a storage device (for example, a non-transitory, computer-readable storage medium), and a communication interface, such as a transceiver, for communicating over a communication network (e.g., wireless) and, optionally, one or more additional communication networks or connections. The electronic processor, the storage device, and the communication interface communicate over one or more communication lines or buses. It should be understood that the computer may include additional components than those described above in various configurations and may perform additional functionality than the functionality described in the present application. For example, in some embodiments, the functionality described herein as being performed by the computer may be distributed among multiple devices, such as multiple computers and servers.

The electronic processor executes instructions stored in the storage device. In particular, the storage device stores an image analyzer. The image analyzer is a software application executable by the electronic processor. As described below, the image analyzer, when executed by the electronic processor, communicates with the camera 136 over the communication networks (through the communication interface) to manage migration of data stored locally on the camera 136 to the one or more remote storage locations (e.g., the storage device in the computer).

The image analyzer receives an input of images generated by the camera 136. The image analyzer can process the images to combine them into a merged image illustrating bead and enzyme location of the samples in the detection vessel 104. For example, see FIG. 6, which illustrates images (C) and (F) with analyzed and merged images. Specifically, image (C) is the analyzed and merged image of images (A) and (B) in FIG. 6. Similarly, image (F) is the analyzed and merged image of images (D) and (E) in FIG. 6.

2. METHODS FOR ANALYTE ANALYSIS

Also provided herein are methods for analyte analysis. The method may involve single molecule counting. In certain embodiments, a method for analyte analysis may involve assessing an analyte of interest present in a sample. In certain embodiments, the assessing may be used for determining presence of and/or concentration of an analyte of interest in a sample. In certain embodiments, the method may also be used for determining presence of and/or concentration of a plurality of different analytes of interest present in a sample.

Provided herein are methods for detecting an analyte of interest in liquid droplet (wherein the analyte of interest is from a test or biological sample). The method includes providing a first liquid droplet containing an analyte of interest, providing a second liquid droplet containing at least one solid support (such as, for example, a magnetic solid support (such as a bead)) which contains a specific binding member that binds to the analyte of interest, using energy to exert a force to manipulate the first liquid droplet (which contains the analyte of interest) with the second liquid (containing the at least one solid support) to create a mixture (also referred to herein as a "reaction mixture"), moving all or at least a portion of the mixture to an array of wells (where one or more wells of the array are of sufficient size to accommodate the at least one solid support), adding at least one detectable label to the mixture before, after or both before or after moving a portion of the mixture to the array of wells and detecting the analyte of interest in the wells. The array of wells is also referred to herein as a "detection vessel".

In some embodiments, the wells can be a microwell array or nanowell array. In some embodiments, the microwell array or nanowell array has a diameter of at least about 4 mm, at least about 5 mm, at least about 6 mm, at least about 7 mm, at least about 8 mm, at least about 9 mm, or at least about 10 mm. In some embodiments, the microwell array has a diameter of 6 mm. In some embodiments, the microwell array or nanowell array contains approximately 100,000 to approximately 1,000,000 wells, approximately 200,000 to approximately 750,000 wells, or approximately 300,000 to approximately 500,000 wells. In some embodiments, the microwell array contains about 100,000, about 200,000, about 300,000, about 350,000, about 375,000, about 400,000, about 425,000, about 450,000, about 475,000, about 500,000, about 600,000, about 700,000, about 800,000, about 900,000, or about 1,000,000 wells. In some embodiments, the microwell array contains 400,000 wells. In some embodiments, the wells can have at least about 1 µM diameter, at least about 2 µM diameter, at least about 3 µM diameter, at least about 4 µM diameter, at least about 5 µM diameter, at least about 6 µM diameter, at least about 7 µM diameter, at least about 8 µM diameter, at least about 9 µM diameter, or at least about 10 µM diameter at the bottom of the well. In some embodiments, the plurality of reaction vessels can be a microwell array or nanowell array having a diameter of 6 mm and containing approximately 400,000 wells having a 5 µm diameter at the bottom of the well.

In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, if magnetic solid supports are used, an electric actuation force and a magnetic field can be applied and applied from opposition directions, relative to the at least a portion of the mixture. In certain other embodiments, the mixture is mixed by moving it: back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the at least one solid support into the array of wells. In certain embodiments, a magnetic field is used to facilitate movement of the mixture and thus, at least one solid support, into one or more wells of the array. In certain embodiments, after the at least one solid supports are loaded into the wells, any solid supports that are not loaded into a well can be removed using routine techniques known in the art. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove the solid supports not bound to any analyte of interest. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method has a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the at least one solid support comprises at least one specific binding member that specifically binds to the analyte of interest. In certain embodiments, the detectable label is added to the mixture before moving at least a portion of the mixture to the array of wells. In certain other embodiments, the detectable label is added to the mixture after the moving of at least a portion of the analyte of interest. In certain embodiments, the detectable label comprises at least one specific binding member that specifically binds to the analyte of interest. In certain embodiments, the detectable label comprises a chromagen, a florescent compound, an enzyme, a chemiluminescent compound or a radioactive compound. In certain embodiments, the specific binding member is a receptor, aptamer or antibody. In certain embodiments, the method further comprises positioning the at least a portion of the mixture over the array of wells using a capillary element configured to facilitate movement of the mixture to the array of wells.

In certain embodiments, when the mixture is a liquid and after the mixture is moved to an array of wells, an aqueous phase is created within the wells. In certain embodiments, the wells can be sealed by the addition of one or more solvents ("solvent well sealing"). A hydrophilic or a hydrophobic solvent can be used. Hydrophilic solvents that can be used include hydrophilic alcohols, hydrophilic ethers, ketones, nitrile solvents, dimethyl sulfoxides, and N,N-dimethylformamides, or mixtures thereof. Examples of hydrophilic alcohols include ethanol, methanol, propanol, and glycerin. Examples of hydrophilic ethers include tetrahydrofuran, polyethylene oxide, and 1,4-dioxane. Examples of ketone includes acetone and methyl ethyl ketone. Examples of the nitrile solvents include acetonitrile. Hydrophobic solvents that can be used include hydrocarbons, unsaturated hydrocarbons, aromatic hydrocarbons, silicone oils, perfluorocarbons, halogen solvents, hydrophobic ionic liquids and mixtures thereof. Examples of saturated hydrocarbons include alkanes, such as decane and hexadecane. Examples of unsaturated hydrocarbon include squalene. Examples of aromatic hydrocarbon include benzene and toluene. Examples of perfluorocarbon encompass Fluorinert®, FC-40, FC-72, FC-84, FC-77, FC-3255, FC-3283, FC-43, FC-70), 3M Novec 4200, 3M Novec 4300, 3M FC-4432, 3M FC-4430, or 3M FC-4434. Examples of halogen solvents encompass chloroform, methylene chloride, and chlorobenzene. The hydrophobic ionic liquid denotes ionic liquid which is not dissociated at least in water. Examples of ionic liquids include 1-butyl-3-methylimidazolium hexafluorophosphate.

Because the hydrophilic or hydrophobic solvent has a density that is heavier than the aqueous phase, after the solvent is added, it moves towards the bottom of the well and displaces the aqueous phase, thus forcing it to the surface and creating a clear separation between the upper aqueous phase and the lower solvent phase. The upper aqueous phase can be removed using routine techniques known in the art.

In certain embodiments, the method described herein is performed using the optical imaging system described in Section 1. In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, the methods described herein are performed using a robotics based assay processing unit.

Provided herein are methods for detecting an analyte of interest in liquid droplet (wherein the analyte of interest is from a test or biological sample). The method includes providing a first liquid droplet containing an analyte of interest, providing a second liquid droplet containing at least one detectable label which contains a specific binding member that binds to the analyte of interest, using energy to exert a force to manipulate the first liquid droplet (which contains the analyte of interest) with the second liquid (containing the at least one solid support) to create a mixture (namely, a reaction mixture containing an analyte/detectable label-specific binding member complex), moving all or at least a portion of the mixture to an array of wells (where one or more wells of the array are of sufficient size to accommodate the at least one solid support), optionally sealing the wells using one or more solvents, and detecting the analyte of interest in the wells. In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, the mixture is mixed by moving it back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the analyte/detectable label-specific binding member complex into the array of wells. In certain embodiments, a magnetic field is used to facilitate movement of the mixture and thus, at least one analyte/detectable label-specific binding member complex into one or more wells of the array. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove any detectable label-specific binding members not bound to any analyte. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method has a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the detectable label is bound to at least one solid support. In certain embodiments, the detectable label comprises a chromagen, a florescent compound, an enzyme, a chemiluminescent compound or a radioactive compound. In certain embodiments, the specific binding member is a receptor, aptamer or antibody. In certain embodiments, the method further comprises positioning the at least a portion of the mixture over the array of wells using a capillary element configured to facilitate movement of the mixture to the array of wells.

In certain embodiments, when the mixture is a liquid and after the mixture is moved to an array of wells, an aqueous phase is created within the wells. In certain embodiments, the wells can be sealed by the addition of one or more solvents as discussed previously herein.

In certain embodiments, the method described herein is performed using the compact digital immunoassay apparatus described herein. In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, method described herein is performed using a Robotics based assay processing unit.

Provided herein are methods for measuring an analyte of interest in liquid droplet (wherein the analyte of interest is from a test or biological sample). The method includes providing a first liquid droplet containing an analyte of interest, providing a second liquid droplet containing at least one solid support (such as, for example, a magnetic solid support (such as a bead)) which contains a specific binding member that binds to the analyte of interest, using energy to exert a force to manipulate the first liquid droplet (which contains the analyte of interest) with the second liquid (containing the at least one solid support) to create a mixture (also referred to herein as a "reaction mixture"), moving all or at least a portion of the mixture to an array of wells (where one or more wells of the array are of sufficient size to accommodate the at least one solid support), adding at least one detectable label to the mixture before, after or both before or after moving a portion of the mixture to the array of wells, optionally sealing the array of wells using one or more solvents, and measuring the analyte of interest in the wells. In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, if magnetic solid supports are used, an electric actuation force and a magnetic field can be applied and applied from opposition directions, relative to the at least a portion of the mixture. In certain other embodiments, the mixture is mixed by moving it: back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the at least one solid support into the array of wells. In certain embodiments, a magnetic field is used to facilitate movement of the mixture and thus, at least one solid support, into one or more wells of the array. In certain embodiments, after the at least one solid supports are loaded into the wells, any solid supports that are not loaded into a well can be removed using routine techniques known in the art. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove the solid supports not bound to any analyte of interest. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method have a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the at least one solid support comprises at least one specific binding member that specifically binds to the analyte of interest. In certain embodiments, the detectable label is added to the mixture before moving at least a portion of the mixture to the array of wells. In certain other embodiments, the detectable label is added to the mixture after the moving of at least a portion of the analyte of interest to the array of wells. In certain embodiments, the detectable label comprises at least one specific binding member that specifically binds to the analyte of interest. In certain embodiments, the detectable label comprises a chromagen, a florescent compound, an enzyme, a chemiluminescent compound or a radioactive compound. In certain embodiments, the specific binding member is a receptor, aptamer or antibody. In certain embodiments, the method further comprises positioning the at least a portion of the mixture over the array of wells using a capillary element configured to facilitate movement of the mixture to the array of wells.

In certain embodiments, when the mixture is a liquid and after the mixture is moved to an array of wells, an aqueous phase is created within the wells. In certain embodiments, the wells can be sealed by the addition of one or more solvents as discussed previously herein.

In certain embodiments, the method described herein is performed using the optical imaging system described in Section 1. In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, method described herein is performed using a Robotics based assay processing unit.

In certain embodiments, the measuring first involves determining the total number of solid supports in the well of the array ("total solid support number"). Next, the number of solid supports in the wells of the array that contain the detectable label are determined, such as, for example, determining the intensity of the signal produced by the detectable label ("positives"). The positives are subtracted from the total solid support number to provide the number of solid supports in the array of wells that do not contain a detectable label or are not detected ("negatives"). Then, the ratio of positives to negatives in the array of wells can be determined and then compared to a calibration curve. Alternatively, digital quantitation using the Poisson equation P(x; µ) as shown below:

$$P(x;\mu)=(e^{-\mu})(\mu^x)/x!$$

where:

e: A is a constant equal to approximately 2.71828,

µ: is the mean number of successes that occur in a specified region, and x: is the actual number of successes that occur in a specified region.

The sample used in the methods described herein may be any test sample containing or suspected of containing an analyte of interest. As used herein, "analyte", "target analyte", "analyte of interest" are used interchangeably and refer to the analyte being measured in the methods and devices disclosed herein. Analytes of interest are further described below.

"Contacting" and grammatical equivalents thereof as used herein refer to any type of combining action which brings a specific binding member into sufficiently close proximity with the analyte of interest in the sample such that a binding interaction will occur if the analyte of interest specific for the specific binding member is present in the sample. Contacting may be achieved in a variety of different ways, including combining the sample with a specific binding member, exposing a target analyte to a specific binding member by introducing the binding member in close proximity to the analyte, and the like.

In certain cases, the first specific binding member may be immobilized on a solid support. As used herein, the term "immobilized" refers to a stable association of the first specific binding member with a surface of a solid support. By "stable association" is meant a physical association between two entities in which the mean half-life of association is one day or more, e.g., under physiological conditions. In certain aspects, the physical association between the two entities has a mean half-life of two days or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

The solid support having a surface on which the specific binding member is immobilized may be any convenient surface in planar or non-planar conformation, such as a surface of a microfluidic chip, an interior surface of a chamber, an exterior surface of a bead (as defined herein), or an interior and/or exterior surface of a porous bead. For example, the first specific binding member may be attached covalently or non-covalently to a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. In certain embodiments, the bead may be a magnetic nanobead, nanoparticle, microbead or microparticle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the contacting step, the sample and the first specific binding member may be incubated for a sufficient period of time to allow for the binding interaction between the specific binding member and analyte to occur. In addition, the incubating may be in a binding buffer that facilitates the specific binding interaction. The binding affinity and/or specificity of the first specific binding member and/or the second specific binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer.

The binding affinity and/or specificity of the first specific binding member and/or the second specific binding member may be measured using the disclosed methods and device described below. In some embodiments, the one aliquot of sample is assayed using one set of conditions and compared to another aliquot of sample assayed using a different set of conditions, thereby determining the effect of the conditions on the binding affinity and/or specificity. For instance, changing or altering the condition can be one or more of removing the target analyte from the sample, adding a molecule that competes with the target analyte or the ligand for binding, and changing the pH, salt concentration, or temperature. Additionally or alternatively, a duration of time can be the variable and changing the condition may include waiting for a duration of time before again performing the detection methods.

The binding buffer may include molecules standard for antigen-antibody binding buffers such as, albumin (e.g., BSA), non-ionic detergents (Tween-20, Triton X-100), and/or protease inhibitors (e.g., PMSF). In certain cases, the binding buffer may be added to the microfluidic chip, chamber, etc., prior to or after adding the sample. In certain cases, the first specific binding member may be present in a binding buffer prior to contacting with the sample. The length of time for binding interaction between the binding member and analyte to occur may be determined empirically and may depend on the binding affinity and binding avidity between the binding member and the analyte. In certain embodiments, the contacting or incubating may be for a period of 5 sec to 1 hour, such as, 10 sec-30 minutes, or 1 minute-15 minutes, or 5 minutes-10 minutes, e.g., 10 sec, 15 sec, 30 sec, 1 minute, 5 minutes, 10 minutes, 15 minutes, 30 minutes, 45 minutes, 1 hour or 2 hours. Other conditions for the binding interaction, such as, temperature, salt concentration, may also be determined empirically or may be based on manufacturer's instructions. For example, the contacting may be carried out at room temperature (21° C.-28° C., e.g., 23° C.-25° C.), 37° C., or 4° C. In certain embodiments, an optional mixing of the sample with the first specific binding member may be carried out during the contacting step.

Following complex formation between the immobilized first specific binding member and the analyte, any unbound analyte may be removed from the vicinity of the first specific binding member along with the sample while the complex of the first specific binding member and the analyte may be retained due to its association with the solid support. Optionally, the solid support may be contacted with a wash buffer to remove any molecules non-specifically bound to the solid support.

After the first contacting step, and the optional removal of sample and/or optional wash steps, the complex of the first specific binding member and the analyte may be contacted with a second specific binding member, thereby leading to the formation of a sandwich complex in which the analyte is bound by the two specific binding members. An optional mixing of the second member with the first specific binding member-analyte complex may be carried out during the second contacting step. In some embodiments, immobilization of the analyte molecules with respect to a surface may aid in removal of any excess second specific binding members from the solution without concern of dislodging the analyte molecule from the surface. In some embodiments, the second specific binding member may include a detectable label comprising one or more signal-producing substances, such as chromagens, fluorescent compounds, chemiluminescent compounds, enzymes, radioactive compounds, and the like.

As noted above, the second contacting step may be carried out in conditions sufficient for binding interaction between the analyte and the second specific binding member. Following the second contacting step, any unbound second specific binding member may be removed, followed by an optional wash step. Any unbound second specific binding member may be separated from the complex of the first specific binding member-analyte-second specific binding member by a suitable means such as, droplet actuation, electrophoresis, electrowetting, dielectrophoresis, electrostatic actuation, electric field mediated, electrode mediated, capillary force, chromatography, centrifugation, aspiration or SAW. Upon removal of any unbound second specific binding member from the vicinity of the complex of the first specific binding member-analyte-second specific binding member, the detectable label attached to the second specific binding member present in the complex of the first specific binding member-analyte-second specific binding member may be separated by a suitable means or may be detected using techniques known in the art. In some embodiments, the detectable label comprises a detectable label comprising one or more signal-producing substances, such as chromagens, fluorescent compounds, enzymes, chemiluminescent compounds, radioactive compounds, and the like.

Alternatively, in some embodiments, if the detectable label comprises a tag, the tag can be cleaved or disassociated from the complex which remains after removal of unbound reagents. For example, the tag may be attached to the second specific binding member via a cleavable linker ("cleavable linker" as described herein. The complex of the first specific binding member-analyte-second specific binding member may be exposed to a cleavage agent that mediates cleavage of the cleavable linker.

As noted herein, the tag may include a nucleic acid. In certain embodiments, the quantification of the analyte does not include determining the identity of the tag by determining identity of at least a portion of the nucleic acid sequence present in the tag. For example, the counting step may not include determining a sequence of the tag. In other embodiments, the tag may not be sequenced, however, identity of the tag may be determined to the extent that one tag may be distinguished from another tag based on a differentiable signal associated with the tag due its size, conformation, charge, amount of charge and the like. Identification of tag may be useful in methods involving simultaneous analysis of a plurality of different analytes in a sample, for example, two, three, four, or more different analytes in a sample.

In certain embodiments, the simultaneous analysis of multiple analytes in a single sample may be performed by using a plurality of different first and second specific binding members where a pair of first and second specific binding members is specific to a single analyte in the sample. In these embodiments, the detectable label associated with the second specific binding member of a first pair of first and second specific binding members specific to a single analyte may be distinguishable from the detectable label associated with the second specific binding member of a second pair of first and second specific binding members specific to a different analyte. As noted above, a first detectable label may be distinguishable from second detectable label based on difference in signal-producing substances, etc.

In some embodiments, the concentration of an analyte in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less.

In some cases, the limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less.

The upper limit of detection (e.g., the upper concentration of an analyte which may be determined in solution) is at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 at least about 100 at least about 1000 at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

In certain embodiments, at least some of the methods described herein may be performed using the optical imaging system described in Section 1. In certain embodiments, at least some steps of the methods described herein may be carried out on a digital integrated microfluidics and analyte detection device, such as the device described herein. In certain embodiments, the methods of the present disclosure are carried out using a digital integrated microfluidics device in conjunction with an analyte detection device. For example, the digital microfluidics device and the analyte detection device may be separate devices and a droplet containing the detectable label may be generated in the microfluidics device and transported to the analyte detection device.

In certain embodiments, the methods of the present disclosure are carried out using a device in which a digital microfluidics module is integrated with an analyte detection device, such as the device described below. In certain embodiments, the digital integrated microfluidics module and the analyte detection device may be reversibly integrated. For example, the two modules may be combined physically to form the integrated device and which device could then be separated into the individual modules. In certain embodiments, the methods of the present disclosure are carried out using a disposable cartridge that includes a microfluidics module with a built-in analyte detection device. Exemplary embodiments of the devices used for performing the methods provided herein are described further in the next section.

Exemplary embodiments of the present method include merging a sample droplet containing an analyte of interest with a droplet containing a first specific binding member that binds to the analyte of interest and that may be immobilized on a solid support (such as magnetic particles or beads). The single merged droplet can be incubated for a period of time sufficient to allow binding of the first specific binding member to the analyte of interest. Optionally, the single droplet may be agitated to facilitate mixing of the sample with the first specific binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away and replaced with a droplet containing a second specific binding member, which second specific binding member can optionally contain a detectable label. An optional wash step may be performed, prior to adding the second specific binding member, by moving a droplet of wash buffer to the location at which the beads are retained using the magnetic force. After a period of time sufficient for the second specific binding member to bind the analyte bound to the first specific binding member, the droplet containing the second specific binding member may be moved away while the beads are retained at the first location. The beads may be washed using a droplet of wash buffer. Following the wash step, the magnetic force may be removed and the droplet containing labeled beads (containing the first specific binding member/analyte/second specific binding member-an optional detectable label) are moved to a detection module such as that described herein. The labeled beads are allowed to settle into an array of wells in the detection module. The beads may settle via gravitational force or by applying electric or magnetic force. Following a wash step to remove any beads not located inside the wells, the wells may be sealed using a solvent (such as a hydrophobic liquid, such as an oil). In the above embodiments, optionally, after the combining, a droplet may be manipulated (e.g., moved back and forth, moved in a circular direction, oscillated, split/ merged, exposed to SAW, etc.) to facilitate mixing of the sample with the assay reagents, such as, the first specific binding member, second specific binding member, etc. In embodiments where the detectable label is an enzyme, a substrate can be added either before or after moving the complex is moved to the array of wells.

The moving of the droplets in the integrated microfluidic and analyte detection device may be carried out using electrical force (e.g., electrowetting, dielectrophoresis, electrode-mediated, opto-electrowetting, electric-field mediated, and electrostatic actuation) pressure, surface acoustic waves and the like. The force used for moving the droplets may be determined based on the specifics of the device, which are described in the following sections, and for the particular device described herein.

In some embodiments, one or more detected signals corresponds to a binding event of a specific binding member to an analyte. In some embodiments, one detected signal corresponds to a binding event of a specific binding member to an analyte. In some embodiments, two or more detected signals correspond to a binding event of a specific binding member to an analyte.

In some embodiments, the solid support comprising the first specific binding member and second specific binding member are added sequentially or simultaneously to the sample.

The detection of the analyte is correlated by the detectable product or detectable label, namely, a signal, generated by the at least one signal generating compound and the at least one signal generating substrate. In some embodiments, the at least one signal generating compound is an enzyme and the at least one signal generating substrate is a substrate for the enzyme. In some embodiments, the substrate for the enzyme is a colorimetric, fluorogenic (non-fluorescent) substrate or a chromogenic substrate. In some embodiments, the detectable signal is a fluorescent signal. For example, the enzyme may be a, polynucleotidase, arginase, adenase, aminopolypeptidase, pepsin, lipases, catalase, tyrosinases, alcohol dehydrogenase, succinic dehydrogenase, diaphorase, glyoxalase, aldolase, glucose oxidase, horseradish peroxidase, galactosidase (such as beta-galactosidase), phosphatases, phosphorylases and hexokinases or combinations thereof. Examples of enzymatic substrates that can be used include a chemiluminescent substrate such as CDP-Star®, (disodium 4-chloro-3-(methoxyspiro{1,2-dioxetane-3,2'-(5'-chloro)tricyclo[3.3.1.1.s-up.3,7]decane}-4-yl)phenyl phosphate), CSPD®, or (disodium 3-(4-methoxyspiro{1,2-dioxetane-3,2-(5'-chloro)tricyclo[3.3.1.1-.sup.3,7]decane}-4-yl)phenyl phosphate); a luminescent substrate such as p-nitrophenyl phosphate, 5-bromo-4-chloro-3-indolyl phosphate (BCIP), 4-nitro blue tetrazolium chloride (NBT), or iodonitrotetrazolium (INT); a fluorescent substrate such as 4-methylumbelliferyl phosphate (4-MUP); and a chromogenic substrate such as 5-bromo-4-chloro-3-indolyl phosphate (BCIP), disodium 5-bromo-6-chloro-indolyl phosphate, or p-nitrophenyl phosphate.

In some aspects, enzymes that can be used include those which contain an inhibitor molecule (such as a protein, peptide, etc.) bound to a site other than the active binding site of the enzyme. Such inhibitor molecules change the conformation of the active binding site of the enzyme and prevent it from binding to the substrate. Examples of inhibitor molecules include protease inhibitors. The inhibitor can be removed from the enzyme using routine techniques known in the art to allow the enzyme to bind to the substrate thus allowing a signal generating reaction to occur.

In some embodiments, the enzyme can convert a non-fluorescent substrate into a fluorescent substrate. In some embodiments, the enzyme can generate color using a chromogenic substrate.

3. SPECIFIC BINDING MEMBERS

As will be appreciated by those in the art, the specific binding members will be determined by the analyte to be analyzed. Specific binding members for a wide variety of target molecules are known or can be readily found or developed using known techniques. For example, when the target analyte is a protein, the specific binding members may include proteins, particularly antibodies or fragments thereof (e.g., antigen-binding fragments (Fabs), Fab' fragments, F(ab')$_2$ fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., Journal of Biomolecular Screening, 14:77-85 (2009)), recombinant VHH single-domain antibodies, and VNAR fragments, disulfide-linked Fvs ("sdFv"), and anti-idiotypic ("anti-Id") antibodies, and functionally active epitope-binding fragments of any of the above, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second specific binding member may be a scaffold protein (e.g., lipocalins) or a receptor. In some cases, specific binding member for protein analytes may be a peptide. For example, when the target analyte is an enzyme, suitable specific binding members may include enzyme substrates and/or enzyme inhibitors which may be a peptide, a small molecule and the like. In some cases, when the target analyte is a phosphorylated species, the specific binding members may comprise a phosphate-binding agent. For example, the phosphate-binding agent may comprise metal-ion affinity media such as those describe in U.S. Pat. No. 7,070,921 and U.S. Patent Application No. 2006/0121544.

When the target molecule is a carbohydrate, potentially suitable capture components (as defined herein) include, for example, antibodies, lectins, and selectins. As will be appreciated by those of ordinary skill in the art, any molecule that can specifically associate with a target molecule of interest may potentially be used as a specific binding member.

For certain embodiments, suitable target analyte/specific binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, the first specific binding member and/or second specific binding member may be attached to a solid support via a linkage, which may comprise any moiety, functionalization, or modification of the support and/or specific binding member that facilitates the attachment of the specific binding member to the support. The linkage between the specific binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s).

In certain embodiments, a solid support may also comprise a protective, blocking, or passivating layer that can eliminate or minimize non-specific attachment of non-capture components (e.g., analyte molecules, specific binding members) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; polymer brushes, and nucleic acids, such as salmon sperm DNA.

Certain embodiments utilize specific binding members that are proteins or polypeptides. As is known in the art, any number of techniques may be used to attach a polypeptide to a wide variety of solid supports. A wide variety of techniques are known to add reactive moieties to proteins, for example, the method outlined in U.S. Pat. No. 5,620,850. Further, methods for attachment of proteins to surfaces are known, for example, see Heller, Acc. Chem. Res. 23:128 (1990).

As explained herein, binding between the specific binding members and the analyte, is specific, e.g., as when the specific binding member and the analyte are complementary parts of a binding pair. In certain embodiments, the specific binding member binds specifically to the analyte. By "specifically bind" or "binding specificity," it is meant that the specific binding member binds the analyte molecule with specificity sufficient to differentiate between the analyte molecule and other components or contaminants of the test sample. For example, the specific binding member, according to one embodiment, may be an antibody that binds specifically to an epitope on an analyte. The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the first specific binding member may be an antigen and the second specific binding member may be a secondary antibody that specifically binds to the target antibody or the first specific binding member may be a secondary antibody that specifically binds to the target antibody and the second specific binding member may be an antigen.

In some embodiments, the specific binding member may be chemically programmed antibodies (cpAbs) (described in Rader (2014) Trends in Biotechnology 32:186-197), bispecific cpAbs, antibody-recruiting molecules (ARMs) (described in McEnaney et al. (2012) ACS Chem. Biol. 7:1139-1151), branched capture agents, such as a triligand capture agent (described in Millward et al. (2011) J. Am. Chem. Soc. 133:18280-18288), engineered binding proteins derived from non-antibody scaffolds, such as monobodies (derived from the tenth fibronectin type III domain of human fibronectin), affibodies (derived from the immunoglobulin binding protein A), DARPins (based on Ankyrin repeat modules), anticalins (derived from the lipocalins bilin-binding protein and human lipocalin 2), and cysteine knot peptides (knottins) (described in Gilbreth and Koide, (2012) Current Opinion in Structural Biology 22:1-8; Banta et al. (2013) Annu. Rev. Biomed. Eng. 15:93-113), WW domains (described in Patel et al. (2013) Protein Engineering, Design & Selection 26(4):307-314), repurposed receptor ligands, affitins (described in Behar et al. (2013) 26:267-275), and/or Adhirons (described in Tiede et al. (2014) Protein Engineering, Design & Selection 27:145-155).

According to one embodiment in which an analyte is a biological cell (e.g., mammalian, avian, reptilian, other vertebrate, insect, yeast, bacterial, cell, etc.), the specific binding members may be ligands having specific affinity for a cell surface antigen (e.g., a cell surface receptor). In one embodiment, the specific binding member may be an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell, the bound cell may then be detected by using a second specific binding member that may be the same as the first specific binding member or may bind to a different molecule expressed on the surface of the cell.

In some embodiments, the binding affinity between analyte molecules and specific binding members should be sufficient to remain bound under the conditions of the assay, including wash steps to remove molecules or particles that are non-specifically bound. In some cases, for example in the detection of certain biomolecules, the binding constant of the analyte molecule to its complementary specific binding member may be between at least about $10^4$ and about $10^6$ $M^{-1}$, at least about $10^5$ and about $10^9$ $M^{-1}$, at least about $10'$ and about $10^9$ $M^{-1}$, greater than about $10^9$ $M^{-1}$, or greater.

4. EXEMPLARY TARGET ANALYTES

As will be appreciated by those in the art, any analyte that can be specifically bound by a first specific binding member and a second specific binding member may be detected and, optionally, quantified using methods and devices of the present disclosure.

In some embodiments, the analyte may be a biomolecule or biological molecule. Non-limiting examples of biomolecules and biological molecules include macromolecules such as, proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, BNP, pro-BNP, NT-ProBNP, CK-MB, Galectin-3, and the like), thyroid markers (e.g., Anti-Tg, Anti-TPO, Free T3, Free T4, T-uptake, Total T3, Total T4, TSH), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, or the like. In some embodiments, the analyte may be a biomarker, such as a biomarker for traumatic brain injury, sepsis, or coagulation, an analyte involved with general chemistry (e.g., ammonia, AST, cholesterol, etc.), a protein (e.g., transferrin, CRP, etc.), an analyte for therapeutic drug monitoring (e.g., Methotrexate), an analyte for transplant (e.g., tacrolimus), a drug of abuse, or a biomarker for genetic disorders.

In certain embodiments, the analyte may be a post-translationally modified protein (e.g., phosphorylated, methylated, glycosylated protein) and the first or the second specific binding member may be an antibody specific to a post-translational modification. A modified protein may be bound to a first specific binding member immobilized on a solid support where the first specific binding member binds to the modified protein but not the unmodified protein. In other embodiments, the first specific binding member may bind to both the unmodified and the modified protein, and the second specific binding member may be specific to the post-translationally modified protein.

In some embodiments, the analyte may be a cell, such as, circulating tumor cell, pathogenic bacteria, viruses (including retroviruses, herpesviruses, adenoviruses, lentiviruses, Filoviruses (e.g., West Nile, Ebola and Zika viruses), hepatitis viruses (e.g., A, B, C, D, and E); HPV, Parvovirus, etc.; spores, etc.

A non-limiting list of analytes that may be analyzed by the methods presented herein include Aβ42 amyloid beta-protein, fetuin-A, tau, secretogranin II, prion protein, Alpha-synuclein, tau protein, neurofilament light chain, parkin, PTEN induced putative kinase 1, DJ-1, leucine-rich repeat kinase 2, mutated ATP13A2, Apo H, ceruloplasmin, Peroxisome proliferator-activated receptor gamma coactivator-1 alpha (PGC-1α), transthyretin, Vitamin D-binding Protein, Active-B12, B12, cortisol, folate, frustosamine, homocysteine, intact PTH, pepsinogen I & II, DHEA-S, Estradiol, hCG, progesterone, prolactin, SHBG, testosterone, proapoptotic kinase R (PKR) and its phosphorylated PKR (pPKR), IL-12p40, CXCL13, IL-8, Dkk-3 (semen), p14 endocan fragment, Serum, ACE2, autoantibody to CD25, hTERT, CAl25 (MUC 16), VEGF, sIL-2, Osteopontin, Human epididymis protein 4 (HE4), Alpha-Fetoprotein, Albumin, albuminuria, microalbuminuria, neutrophil gelatinase-associated lipocalin (NGAL), Cystatin C, interleukin 18 (IL-18), Kidney Injury Molecule-1 (KIM-1), Liver Fatty Acid Binding Protein (L-FABP), LMP1, BARF1, IL-8, BRAF, CCNI, EGRF, FGF19, FRS2, GREB1, and LZTS1, alpha-amylase, carcinoembryonic antigen (CEA), CA 125, thioredoxin, beta-2 microglobulin levels—monitor activity of the virus, tumor necrosis factor-alpha receptors—monitor activity of the virus, Alpha-fetoprotein (AFP), CA15-3, CA 19-9, CYFRA 21-1, HE-4, PIVKA-11, ProGRP, SCC, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin 015, insulin, plasma C-peptide, glycosylated hemoglobin (HBA1c), C-Reactive Protein (CRP), Interleukin-6 (IL-6), ARHGDIB (Rho GDP-dissociation inhibitor 2), CFL1 (Cofilin-1), PFN1 (profilin-1), GSTP1 (Glutathione S-transferase P), S100A11 (Protein 5100-A11), PRDX6 (Peroxiredoxin-6), HSPE1 (10 kDa heat shock protein, mitochondrial), LYZ (Lysozyme C precursor), GPI (Glucose-6-phosphate isomerase), HIST2H2AA (Histone H2A type 2-A), GAPDH (Glyceraldehyde-3-phosphate dehydrogenase), HSPG2 (Basement membrane-specific heparan sulfate proteoglycan core protein precursor), LGALS3BP (Galectin-3-binding protein precursor), CTSD (Cathepsin D precursor), APOE (Apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER aka RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm's Tumor-1 protein, Aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, etc.

Exemplary targets may be measured in a sample such as an environmental sample, a biological sample obtained from a patient or subject in need using the subject methods include: drugs of abuse (e.g. cocaine), protein biomarkers (including, but not limited to, Nucleolin, nuclear factor-kB essential modulator (NEMO), CD-30, protein tyrosine kinase 7 (PTK7), vascular endothelial growth factor (VEGF), MUC1 glycoform, immunoglobulin μ Heavy Chains (IGHM), Immunoglobulin E, αvβ3 integrin, α-thrombin, HIV gp120, NF-κB, E2F transcription factor, HER3, Plasminogen activator inhibitor, Tenascin C, CXCL12/SDF-1, prostate specific membrane antigen (PSMA), gastric cancer cells, HGC-27; cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, pancreatic cancer cell line (Mia-PaCa-2), and infectious agents (including, but not limited to, *Mycobacterium tuberculosis, Staphylococcus aureus, Shigella dysenteriae, Escherichia coli* O157:H7, Campylobacter jejuni, Listeria monocytogenes, Pseudomonas aeruginosa, Salmonella O8, and *Salmonella enteritidis*).

Exemplary targets that may be measured in a sample obtained from a patient or subject in need using the subject methods include, but are not limited to: HBV core capsid protein, CDK2, E2F transcription factor, Thymidylate synthase, Ras, EB1, and Receptor for Advanced Glycated End products (RAGE).

5. SAMPLES

As used herein, "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, fluid samples, e.g., water supplies, etc.), an animal, e.g., a mammal, a plant, or any combination thereof. In a particular example, the source of an analyte is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of an analyte molecule is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

In certain embodiments, the analyte is not amplified (i.e., the copy number of the analyte is not increased) prior to the measurement of the analyte. For example, in cases where the analyte is DNA or RNA, the analyte is not replicated to increase copy numbers of the analyte. In certain cases, the analyte is a protein or a small molecule.

6. VARIATIONS ON METHODS

The disclosed methods of determining the presence or amount of analyte of interest present in a sample may be as described above. The methods may also be adapted in view of other methods for analyzing analytes. Examples of well-known variations include, but are not limited to, immunoassay, such as sandwich immunoassay (e.g., monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

(a) Immunoassay

The analyte of interest, and/or peptides or fragments thereof, may be analyzed using an immunoassay. The presence or amount of analyte of interest can be determined using the herein-described antibodies and detecting specific binding to analyte of interest. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, one signal generating compound or signal generating substrate is attached to the capture antibody and the detection antibody. Alternately, a microparticle employed for capture, also can function for detection.

A homogeneous format may be used. For example, after the test sample is obtained from a subject, a mixture is prepared. The mixture contains the test sample being assessed for analyte, a first specific binding partner, and a second specific binding partner. The order in which the test sample, the first specific binding partner, and the second specific binding partner are added to form the mixture is not critical. The test sample is simultaneously contacted with the first specific binding partner and the second specific binding partner. In some embodiments, the first specific binding partner and any analyte of interest contained in the test sample may form a first specific binding partner-analyte of interest-antigen complex and the second specific binding partner may form a first specific binding partner-analyte of interest-second specific binding partner complex. In some embodiments, the second specific binding partner and any analyte of interest contained in the test sample may form a second specific binding partner-analyte of interest-antigen complex and the first specific binding partner may form a first specific binding partner-analyte of interest-second specific binding partner complex. Moreover, the second specific binding partner is labeled with or contains a detectable label as described herein.

A heterogeneous format may be used. For example, after the test sample is obtained from a subject, a first mixture is prepared. The mixture contains the test sample being assessed for analyte of interest and a first specific binding partner, wherein the first specific binding partner and any analyte of interest contained in the test sample form a first specific binding partner-analyte of interest complex. Preferably, the first specific binding partner is an anti-analyte of interest antibody or a fragment thereof. The order in which the test sample and the first specific binding partner are added to form the mixture is not critical. Preferably, the first specific binding partner is immobilized on a solid support. The solid support used in the immunoassay (for the first specific binding partner and, optionally, the second specific binding partner) can be any solid support known in the art, such as, but not limited to, a magnetic particle, a bead a nanobead, a microbead, a nanoparticle, a microparticle, a membrane, a scaffolding molecule, a film, a filter paper, a disc, or a chip (e.g., a microfluidic chip). In those embodiments where the solid support is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte of interest complex is formed, any unbound analyte of interest is removed from the complex using any technique known in the art. For example, the unbound analyte of interest can be removed by washing. Desirably, however, the first specific binding partner is present in excess of any analyte of interest present in the test sample, such that all analyte of interest that is present in the test sample is bound by the first specific binding partner.

After any unbound analyte of interest is removed, a second specific binding partner is added to the mixture to form a first specific binding partner-analyte of interest-second specific binding partner complex. The second specific binding partner is preferably an anti-analyte of interest antibody that binds to an epitope on analyte of interest that differs from the epitope on analyte of interest bound by the first specific binding partner. Moreover, also preferably, the second specific binding partner is labeled with or contains a signal generating compound or signal generating substrate, as described above.

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

(b) Sandwich Immunoassay

The sandwich immunoassay measures the amount of antigen between two layers of antibodies (i.e., a capture antibody (i.e., at least one capture antibody) and a detection antibody (i.e. at least one detection antibody). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a test sample. More specifically, the at least two antibodies bind to certain epitopes of analyte of interest or an analyte of interest fragment forming an immune complex which is referred to as a "sandwich". One or more antibodies can be used to capture the analyte of interest in the test sample (these antibodies are frequently referred to as a "capture" antibody or "capture" antibodies), and one or more antibodies with a signal generating compound or signal generating substrate that also bind the analyte of interest (these antibodies are frequently referred to as the "detection" antibody or "detection" antibodies) can be used to complete the sandwich. In a sandwich assay, the binding of an antibody to its epitope desirably is not diminished by the binding of any other antibody in the assay to its respective epitope. In other words, antibodies are selected so that the one or more first antibodies brought into contact with a test sample suspected of containing analyte of interest do not bind to all or part of an epitope recognized by the second or subsequent antibodies, thereby interfering with the ability of the one or more second detection antibodies to bind to the analyte of interest. The capture antibody described above is an example of a capture molecule. The detection antibody described above is an example of a detection molecule.

In one embodiment, a test sample suspected of containing analyte of interest can be contacted with at least one capture antibody (or antibodies) and at least one detection antibodies either simultaneously or sequentially. In the sandwich assay format, a test sample suspected of containing analyte of interest (membrane-associated analyte of interest, soluble analyte of interest, fragments of membrane-associated analyte of interest, fragments of soluble analyte of interest, variants of analyte of interest (membrane-associated or soluble analyte of interest) or any combinations thereof) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the test sample.

Optionally, prior to contacting the test sample with the at least one first capture antibody, the at least one capture antibody can be bound to a solid support which facilitates the separation the antibody-analyte of interest complex from the test sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the test sample suspected of containing analyte of interest is brought into contact with the at least one capture antibody, the test sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a signal generating compound or signal generating substrate. The signal generating compound or signal generating substrate can be bound to the at least one detection antibody prior to, simultaneously with or after the formation of the capture antibody (antibodies)-analyte of interest-detection antibody (antibodies) complex.

The order in which the test sample and the specific binding partner(s) are added to form the mixture for assay is not critical. If the first specific binding partner is attached to the signal generating compound or signal generating substrate, then signal generating compound or signal generating substrate-attached first specific binding partner-analyte of interest complexes form. Alternatively, if a second specific binding partner is used and the second specific binding partner is attached to the signal generating compound or signal generating substrate, then signal generating compound or signal generating substrate-attached complexes of first specific binding partner-analyte of interest-second specific binding partner form. Any unbound specific binding partner, whether labeled or unlabeled, can be removed from the mixture using any technique known in the art, such as washing.

Next, signal, indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

(c) Forward Competitive Inhibition

In a forward competitive format, an aliquot of labeled analyte of interest of a known concentration is used to compete with analyte of interest in a test sample for binding to analyte of interest antibody.

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be attached with a signal generating compound or signal generating substrate. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a signal generating compound or signal generating substrate while the other antibody-analyte of interest complex does not contain a signal generating compound or signal generating substrate. The antibody-analyte of interest complex can be, but does not have to be, separated from the remainder of the test sample prior to quantification of the detectable product or detectable label. Regardless of whether the antibody-analyte of interest complex is separated from the remainder of the test sample, the amount of detectable product or detectable label (e.g., detectable signal) in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above. If helpful, determination can be done by comparing the quantity of detectable product or detectable label (e.g., detectable signal) in the antibody-analyte of interest complex to a standard curve. The standard curve can be generated using serial dilutions of analyte of interest (such as membrane-associated analyte of interest, soluble analyte of interest, fragments of soluble analyte of interest, variants of analyte of interest (membrane-associated or soluble analyte of interest) or any combinations thereof) of known concentration, where concentration is determined by mass spectroscopy, gravimetrically and by other techniques known in the art.

Optionally, the antibody-analyte of interest complex can be separated from the test sample by binding the antibody to a solid support, such as the solid supports discussed above in connection with the sandwich assay format, and then removing the remainder of the test sample from contact with the solid support.

(d) Reverse Competition Assay

In a reverse competition assay, an immobilized analyte of interest can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a signal generating compound or signal generating substrate while the other analyte of interest-antibody complex is not immobilized and contains signal generating compound or signal generating substrate. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of signal generating compound or signal generating substrate in the immobilized analyte of interest-antibody complex is then quantified. The concentration of analyte of interest in the test sample can then be determined by comparing the quantity of detectable signal as described above. If helpful, this can be done with use of a standard curve. The standard curve can be generated using serial dilutions of analyte of interest or analyte of interest fragment of known concentration, where concentration is determined by mass spectroscopy, gravimetrically and by other techniques known in the art.

(e) One-Step Immunoassay or Capture on the Fly Assay

In a one-step immunoassay or capture on the fly assay, a solid substrate is pre-coated with an immobilization agent. The capture agent, the analyte and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In some embodiments, a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest. The second specific binding member comprises a signal generating compound or signal generating substrate and binds to an analyte of interest. The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the signal generating compounds or signal generating substrates detected. An optional wash step may be employed before the detection. In certain embodiments, in a one-step assay more than one analyte may be measured. In certain other embodiments, more than two specific binding members can be employed. In certain other embodiments, multiple signal generating compounds or signal generating substrates can be added. In certain other embodiments, multiple analytes of interest can be detected.

The use of a one step immunoassay or capture on the fly assay can be done in a variety of formats as described herein, and known in the art. For example the format can be a sandwich assay such as described above, but alternately can be a competition assay, can employ a single specific binding member, or use other variations such as are known.

Combination Assays (Co-Coating of Microparticles with Ag/Ab)

In a combination assay, a solid substrate, such as a microparticle is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacteria, or a portion thereof. The methods also may be used for measuring analyte present in a biological sample. The methods also may be used in blood screening assays to detect a target analyte. The blood screening assays may be used to screen a blood supply.

7. MULTIPLEXING

The methods may include one or more (or alternately two or more) specific binding members to detect one or more (or alternately two or more) target analytes in the sample in a multiplexing assay. Each of the one or more (or alternately two or more) specific binding members binds to a different target analyte and each specific binding member is conjugated to a different signal generating compound or signal generated substrate. For example, a first specific binding member binds to a first target analyte, a second specific binding member binds to a second target analyte, a third specific binding member binds to a third target analyte, etc.

and the first specific binding member is labeled with a first signal generating compound or first signal generating substrate, the second specific binding member is labeled with a second signal generating compound or second signal generating substrate, the third specific binding member is labeled with a third signal generating compound or a third signal generating substrate, etc. In some embodiments, the conditions of the sample can be changed at various times during the assay, allowing detection of the first signal generating compound or first signal generating substrate, the second signal generating compound or second signal generating substrate, the third signal generating compound or third signal generating substrate, etc., thereby detecting one or more (or alternately two or more) target analytes. In some embodiments, the one or more (or alternately two or more) signal generating compounds or signal generating substrates are detected simultaneously. In some embodiments, the one or more (or alternately two or more) signal generating compounds or signal generating substrates are detected consecutively. In some embodiments, the one or more (or alternately two or more) signal generating compounds or signal generating substrates generates a different detectable signal, such as a different wavelength of fluorescence signal.

Alternatively, each of the one or more (or alternately two or more) specific binding members binds to a different target analyte and each specific binding member is conjugated to a different solid support, such as a different fluorophore bead. For example, a first specific binding member binds to a first target analyte, a second specific binding member binds to a second target analyte, a third specific binding member binds to a third target analyte, etc., the first specific binding member is labeled with a first signal generating compound or first signal generating substrate, the second specific binding member is labeled with a second signal generating compound or second signal generating substrate, the third specific binding member is labeled with a third signal generating compound or a third signal generating substrate, etc., and the first specific binding member is immobilized on a first solid support, the second specific binding member is immobilized on a second solid support, the third specific binding member is immobilized on a third solid support, etc. In some embodiments, the one or more (or alternately two or more) signal generating compounds or signal generating substrates generates a different detectable signal, such as a different wavelength or fluorescence signal, and the different solid supports is detected simultaneously or consecutively.

In some embodiments, a first specific binding member binds to a first target analyte, a second specific binding member binds to a second target analyte, a third specific binding member binds to a third target analyte, etc., the first specific binding member, the second specific binding member, the third specific binding member, etc. are labeled with a signal generating compound or a signal generating substrate, and the first specific binding member is immobilized on a first solid support, the second specific binding member is immobilized on a second solid support, the third specific binding member is immobilized on a third solid support, etc. In some embodiments, the signal generating compounds or signal generating substrates generates a detectable signal, such as a different wavelength or fluorescence signal, and the different solid supports is detected simultaneously or consecutively.

8. KITS

Also provided herein is a kit for use in performing the above-described methods. The kit may include instructions for analyzing the analyte with the disclosed methods. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, "instructions" may include the address of an internet site that provides the instructions.

Alternatively or additionally, the kit may comprise a calibrator or control, e.g., purified, and optionally lyophilized analyte of interest or in liquid, gel or other forms, and/or at least one container (e.g., tube, microtiter plates or strips) for use with the methods described above, and/or a buffer, such as an assay buffer or a wash buffer, either one of which can be provided as a concentrated solution. In some embodiments, the kit comprises all components, i.e., reagents, standards, buffers, diluents, etc., which are necessary to perform the assay. The instructions also can include instructions for generating a standard curve.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay. Exemplary concentration ranges for the reference standards include but are not limited to, for example: about 10 fg/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 pg/mL, about 20 pg/mL, about 50 pg/mL, about 75 pg/mL, about 100 pg/mL, about 150 pg/mL, about 200 pg/mL, about 250 pg/mL, about 500 pg/mL, about 750 pg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1000 µg/mL, about 2000 µg/mL, about 3000 µg/mL, about 4000 µg/mL, about 5000 µg/mL, about 6000

μg/mL, about 7000 μg/mL, about 8000 μg/mL, about 9000 μg/mL, or about 10000 μg/mL.

Any specific binding members, which are provided in the kit may incorporate an at least one signal generating compound, one or more signal generating substrates, or the like, or the kit can include reagents for labeling the specific binding members or reagents for detecting the specific binding members and/or for labeling the analytes or reagents for detecting the analyte. If desired, the kit can contain one or more different signal generating compounds and/or signal generating or substrates. The specific binding members, calibrators, and/or controls can be provided in separate containers or pre-dispensed into an appropriate assay format.

The kit may include one or more specific binding members, for example, to detect one or more target analytes in the sample in a multiplexing assay. The number of different types of specific binding members in the kit may range widely depending on the intended use of the kit. The number of specific binding members in the kit may range from 1 to about 10, or higher. For example, the kit may include 1 to 10 specific binding members, 1 to 9 specific binding members, 1 to 8 specific binding members, 1 to 7 specific binding members, 1 to 6 specific binding members, 1 to 5 specific binding members, 1 to 4 specific binding members, 1 to 3 specific binding members, 1 to 2 specific binding members, 2 to 10 specific binding members, 2 to 9 specific binding members, 2 to 8 specific binding members, 2 to 7 specific binding members, 2 to 6 specific binding members, 2 to 5 specific binding members, 2 to 4 specific binding members, 3 to 10 specific binding members, 3 to 9 specific binding members, 3 to 8 specific binding members, 3 to 7 specific binding members, 3 to 6 specific binding members, 3 to 5 specific binding members, 3 to 4 specific binding members, 4 to 10 specific binding members, 4 to 9 specific binding members, 4 to 8 specific binding members, 4 to 7 specific binding members, 4 to 6 specific binding members, 5 to 10 specific binding members, 5 to 9 specific binding members, 5 to 8 specific binding members, 5 to 7 specific binding members, 5 to 6 specific binding members, 6 to 10 specific binding members, 6 to 9 specific binding members, 6 to 8 specific binding members, 6 to 7 specific binding members, 7 to 10 specific binding members, 7 to 9 specific binding members, 7 to 8 specific binding members, 8 to 10 specific binding members, 8 to 9 specific binding members, or 9 to 10 specific binding members. Each of the one or more specific binding members may bind to a different target analyte and each specific binding member may be associated with a different signal generating compound and/or signal generating substrate. For example, the kit may include a first specific binding member that binds to a first target analyte, a second specific binding member that binds to a second target analyte, a third specific binding member that binds to a third target analyte, etc. and the first specific binding member is associated with a first signal generating compound and/or first signal generating substrate, the second specific binding member is associated with a second signal generating compound and/or second signal generating substrate, the third specific binding member is associated with a third signal generating compound and/or third signal generating substrate, etc. In addition to the one or more specific binding members, the kits may further comprise one or more additional assay components, such as suitable buffer media, and the like. The kits may also include a device for detecting and measuring the signal generating compound and/or signal generating substrate, such as those described supra. Finally, the kits may comprise instructions for using the specific binding members in methods of analyte detection according to the subject invention, where these instructions for use may be present on the kit packaging and/or on a package insert.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container for a urine, saliva, plasma, cerebrospinal fluid, or serum sample, or appropriate container for storing, transporting or processing tissue so as to create a tissue aspirate). Where appropriate, the kit optionally also can contain reaction vessels, mixing vessels, and other components that facilitate the preparation of reagents or the test sample. The kit can also include one or more sample collection/acquisition instruments for assisting with obtaining a test sample, such as various blood collection/transfer devices such as microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or canula, for obtaining, storing or aspirating tissue samples; or the like. The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laproscopic biopsies.

If desired, the kit can contain a solid support, such as a magnetic particle, bead, membrane, scaffolding molecule, film, filter paper, disc, or chip.

If desired, the kit can further comprise one or more components, alone or in further combination with instructions, for assaying the test sample for another analyte, which can be a biomarker, such as a biomarker of a disease state or disorder, such as infectious disease, cardiac disease, metabolic disease, thyroid disease, etc.

9. EXAMPLES

Example 1

FIG. 4 illustrates a microchamber array for digital immunoassay and a mechanism of fluorescent signal amplification by an enzymatic reaction. In this example, the bead diameter was ~2.7 um, the well diameter/depth was ~4 um/~4 um, the enzyme was alkaline phosphatase, the fluorogenic substrate was fluorescein diphosphate, and the signal amplification was for 90 min at RT.

Figure 6:
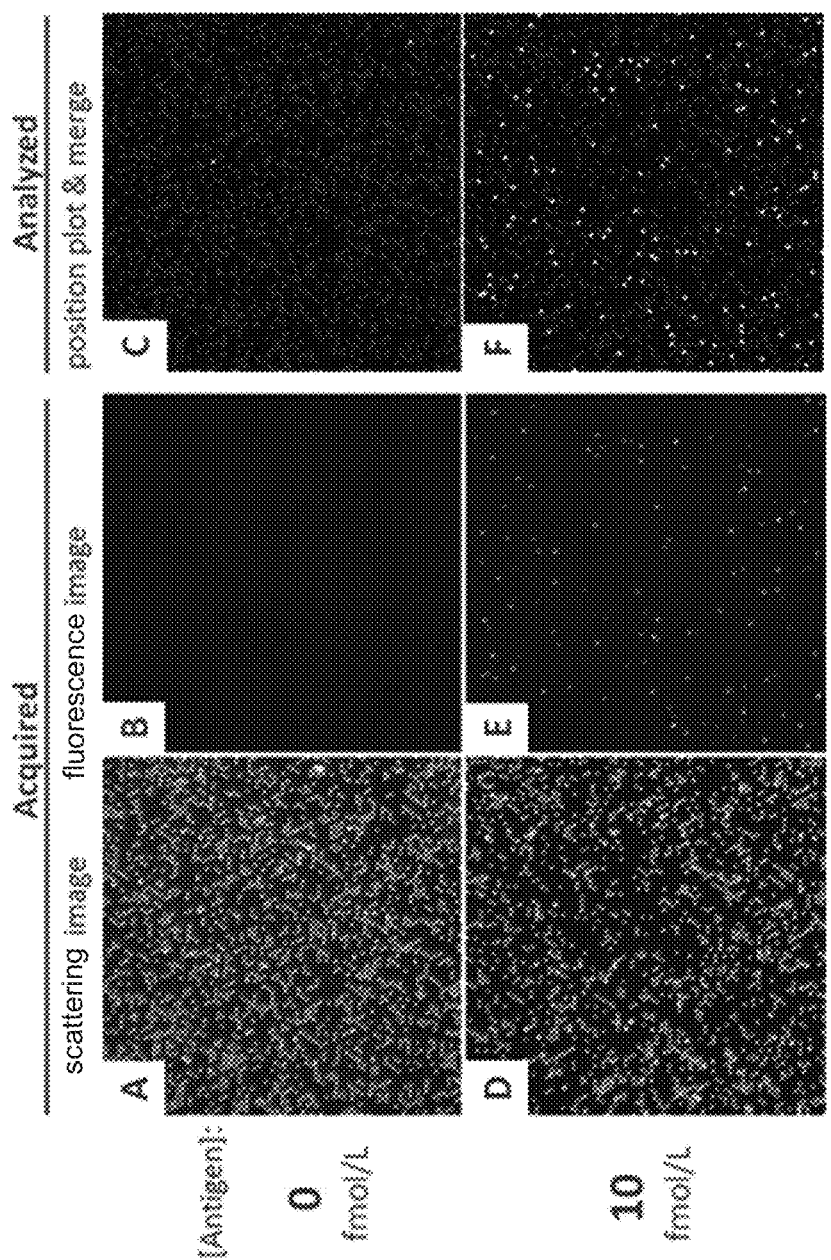
FIG. 6 illustrates images acquired by an optical imaging system illustrated in FIG. 5.
Figure 7:
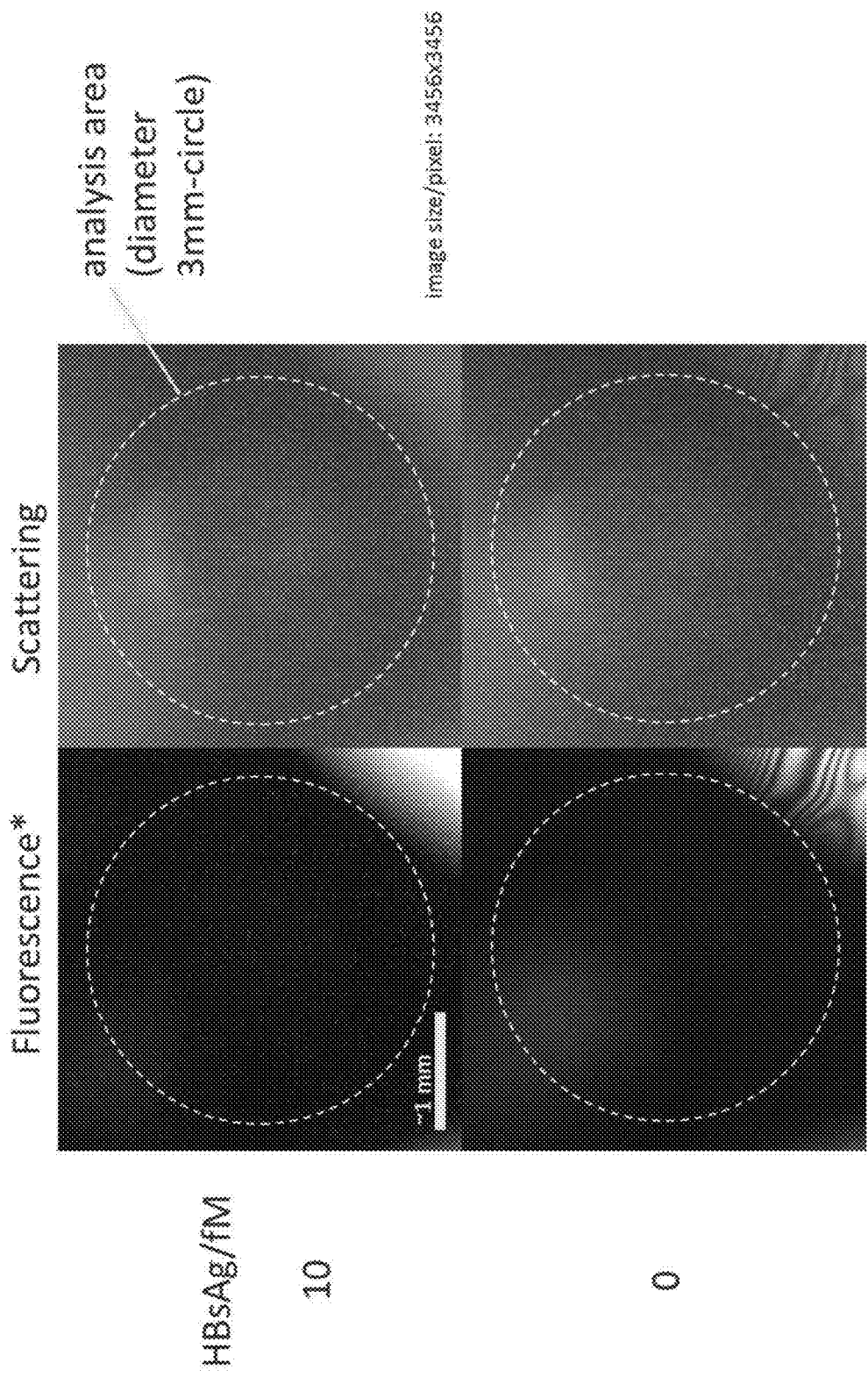
FIG. 7 illustrates images acquired by an optical imaging system illustrated in FIG. 5.
Figure 8:
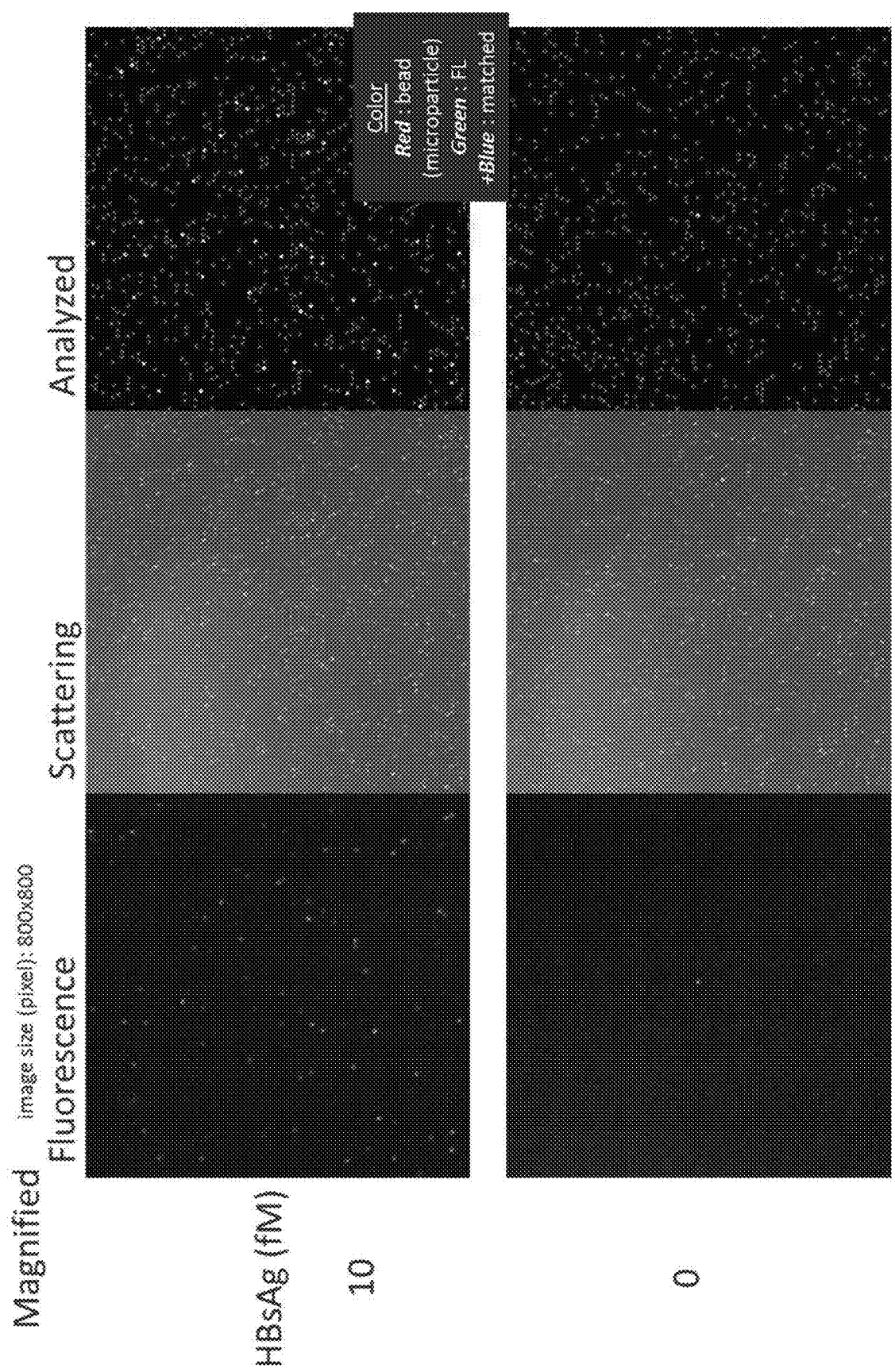
FIG. 8 illustrates images acquired by an optical imaging system illustrated in FIG. 5.
Figure 9:
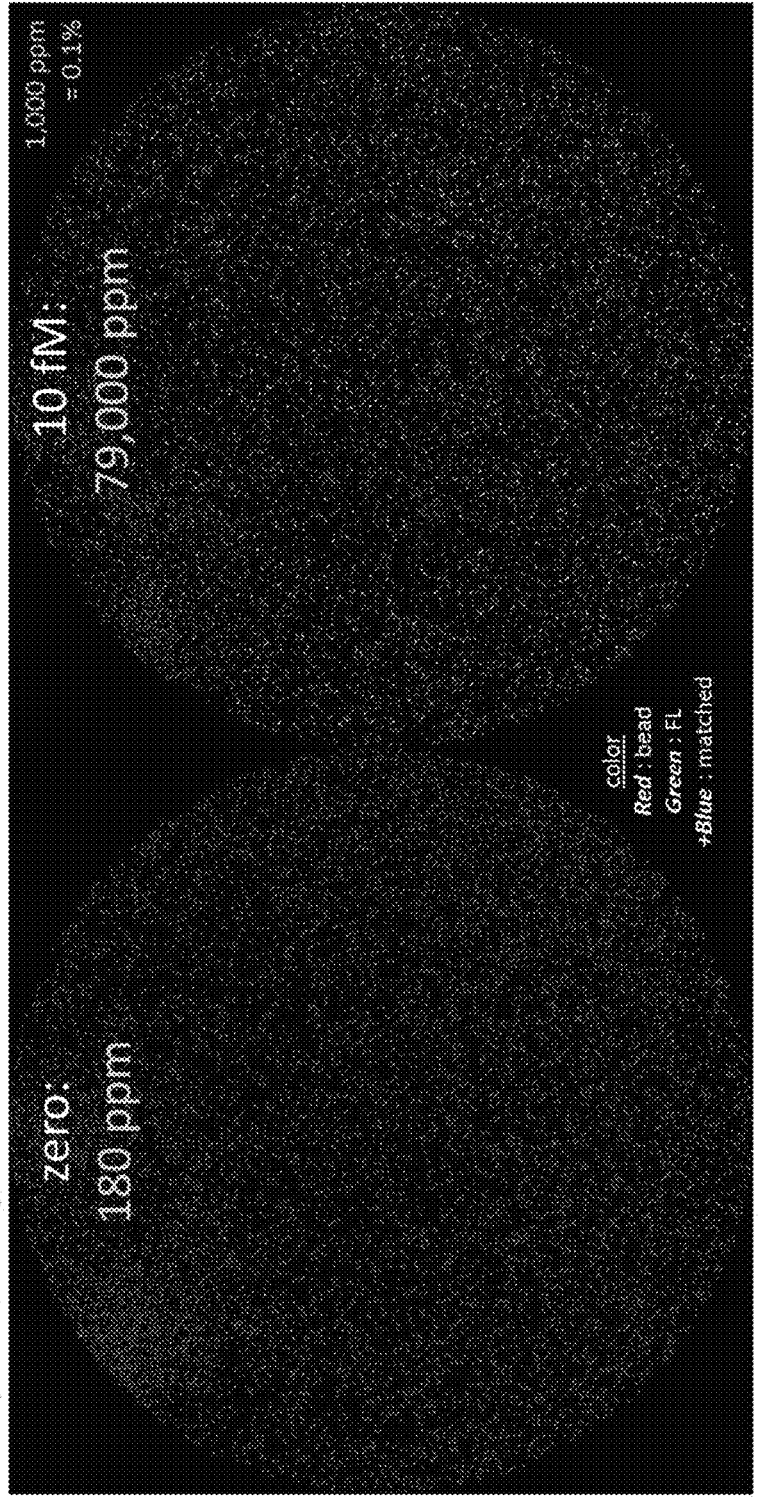
FIG. 9 illustrates images acquired by an optical imaging system illustrated in FIG. 5.
Figure 10:
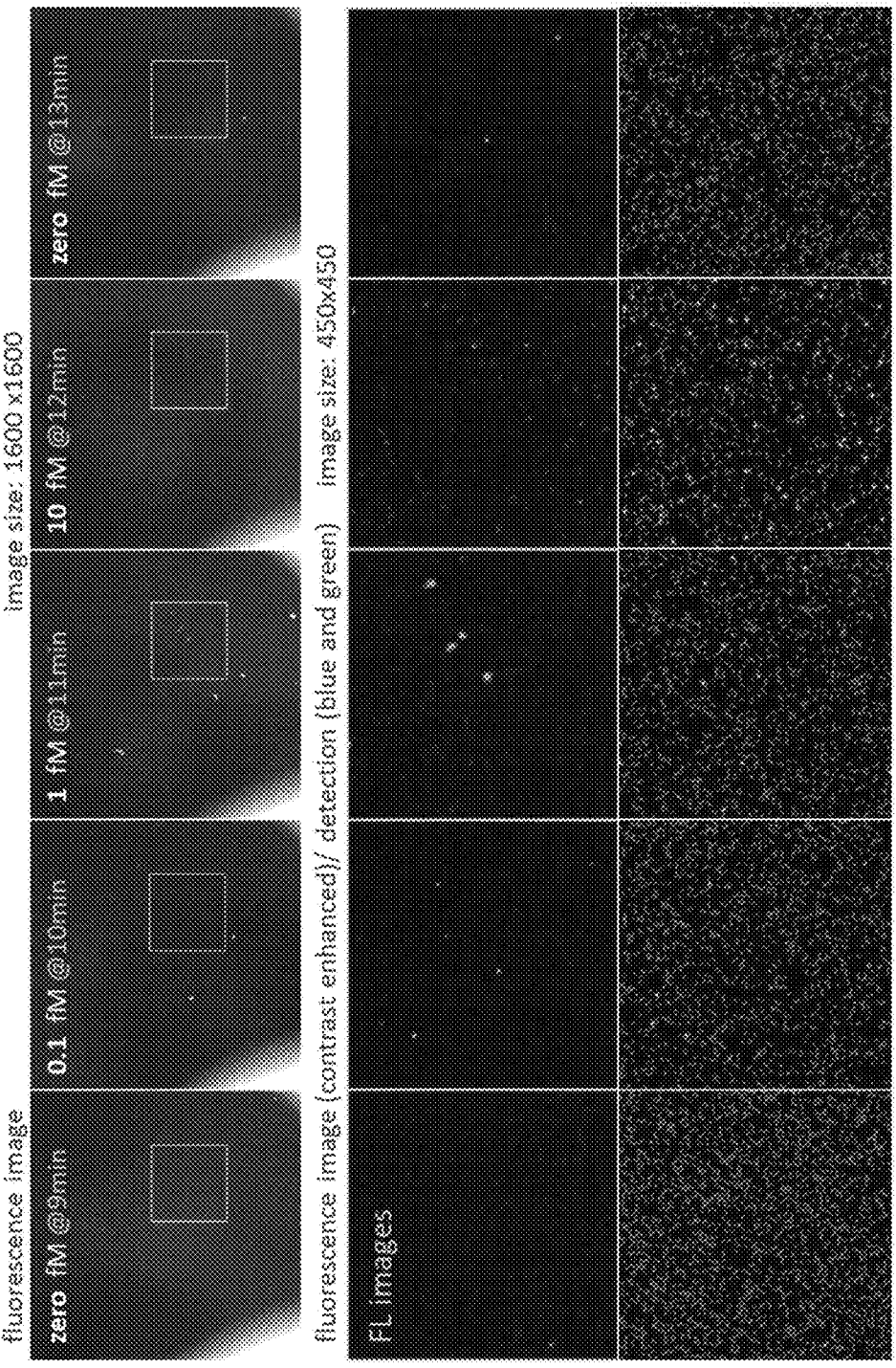
FIG. 10 illustrates images acquired by an optical imaging system illustrated in FIG. 5.
Figure 11:
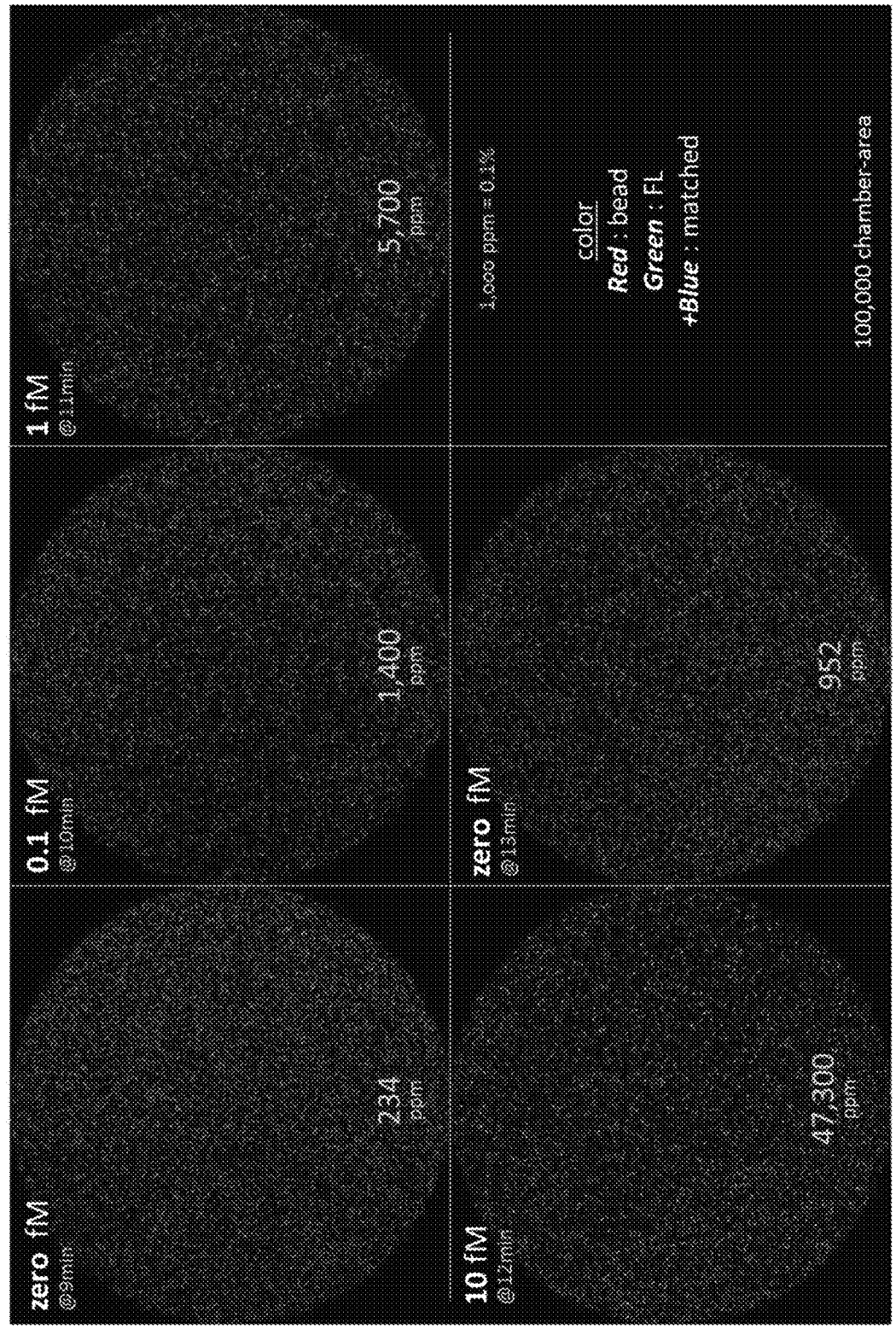
FIG. 11 illustrates images acquired by an optical imaging system illustrated in FIG. 5.

To evaluate the usefulness of the digital ELISA immunoassay, a handheld (~10×10×12 in cm) optical imaging system based on embodiments of the invention was developed. In the demonstration, zero and 10 femto M of antigen solution (recombinant HBsAg) was applied. The first light source applied to the detection vessel resulted in the images (A) and (D), respectively, shown in FIG. 6. The second light source applied to the detection vessel resulted in the images (B) and (E), respectively, shown in FIG. 6. The image analyzer combined the images (A) with (B) that resulted in image (C) and combined the images (D) with (E) that resulted in image (F) as shown in FIG. 6. Images (C) and (F) illustrate detected positions of "only bead" and "bead-and-enzyme" plotted by gray and white dots, respectively; the white dot is identified to an immune-complex signal. The performance of the handheld detector showed good performance—capturing a 100,000 chamber-area in an image—on the digital assay.

Example 2

Digital Immunoassay Optical Detection of HBsAg (Hepatitis B Virus Surface Antigen)

Anti-HBsAg mouse monoclonal antibodies (prepared in-house) were coated onto 3 μm diameter paramagnetic microparticles (Agilent Technologies) surface with EDC (1-ethyl-3-3-Dimethylaminopropyl) to prepare capture antibodies. After the washing, the coated paramagnetic microparticles were added into buffer solution including protein.

Anti HBsAg goat polyclonal antibodies (prepared in-house) were conjugated with alkaline phosphatase (Abbott) using a standard chemical reaction known in the art to prepare detection antibodies. The conjugated antibodies were purified using a routine gel-filtration method known in the art. The purified conjugated antibodies were diluted into buffer solution including protein.

50 μL of the anti-HBsAg antibody microparticle solution and 504, of alkaline phosphatase conjugated anti-HBsAg antibody solution were incubated with 75 μL of human serum (with or without HBsAg). After incubation for 18 minutes at 37 degrees C., the beads were washed with buffer solutions, and mixed with MUP or FDP solution, then loaded into a well (6 mm diameter) that had a microwell array at the bottom (approximately 400,000 of 5 μm diameter wells (femtoliter chamber)). A heavy fluorinated oil (such as, for example, FC-40) was added over the top of the well and the aqueous phase and oil phase were changed. The aqueous phase (top phase) was removed and the well was set with the handheld optical imaging system described herein.

Images (pictures) taken with the optical system are shown in FIGS. 7-11. The microparticles were detected by scattering image detection. The femtoliter chamber which has antibody coated microparticle-HBsAg-Alkaline phosphate conjugated antibody complex (HBsAg immune-complex) was detected by fluorescent image detection. The detected signals were analyzed using the Image J software to count number of microparticle and number of femtoliter chambers which has HBsAg immune-complex.

Example 3

FIG. 4 illustrates a microchamber array for digital immunoassay and a mechanism of fluorescent signal amplification by an enzymatic reaction. In this example, the bead diameter was ~2.7 um and beads included a mixture of Qdot625 (Ex/Em:blue/red)-coated and non-coated (the ratio was approximately 10%), the well diameter/depth was ~4 um/~4 um. All beads and red fluorescence of Qdot-coated beads were visualized by light-scattering and fluorescence imaging, respectively.

To evaluate the usefulness of fluorescence imaging for the digital ELISA immunoassay, a handheld (~10×10×12 in cm) optical imaging system based on embodiments of the invention were utilized. In this example, the single emission filter was a 515 nm longpass type of filter (e.g., Semrok515LP). In the demonstration, 10% of a binary mixture of the red fluorescent and non-fluorescent beads was applied.

The imaging scheme utilized demonstrated that the emission filter did not need to be changed. The imaging scheme utilized a first autofocus step using the first light source which included a green LED (525 nm) and then applied the first light source to the detection vessel for scattering and bead imaging. This resulted in the image (A) shown in FIG. 12. In the next step, the second light source, which included a blue LED (450 nm), was applied to the detection vessel to excite the samples in the detection vessel. This resulted in the fluorescence image (B) shown in FIG. 12. Next, the chromatic aberration was refreshed to include a red LED (625 nm) as the first light source. An autofocus was performed with this refreshed first light source and then applied to the detection vessel for scattering. This resulted in the image (C) shown in FIG. 12. The second light source (the blue LED) was applied to the detection vessel to excite the samples, which resulted in image (D) shown in FIG. 12.

Figure 12:
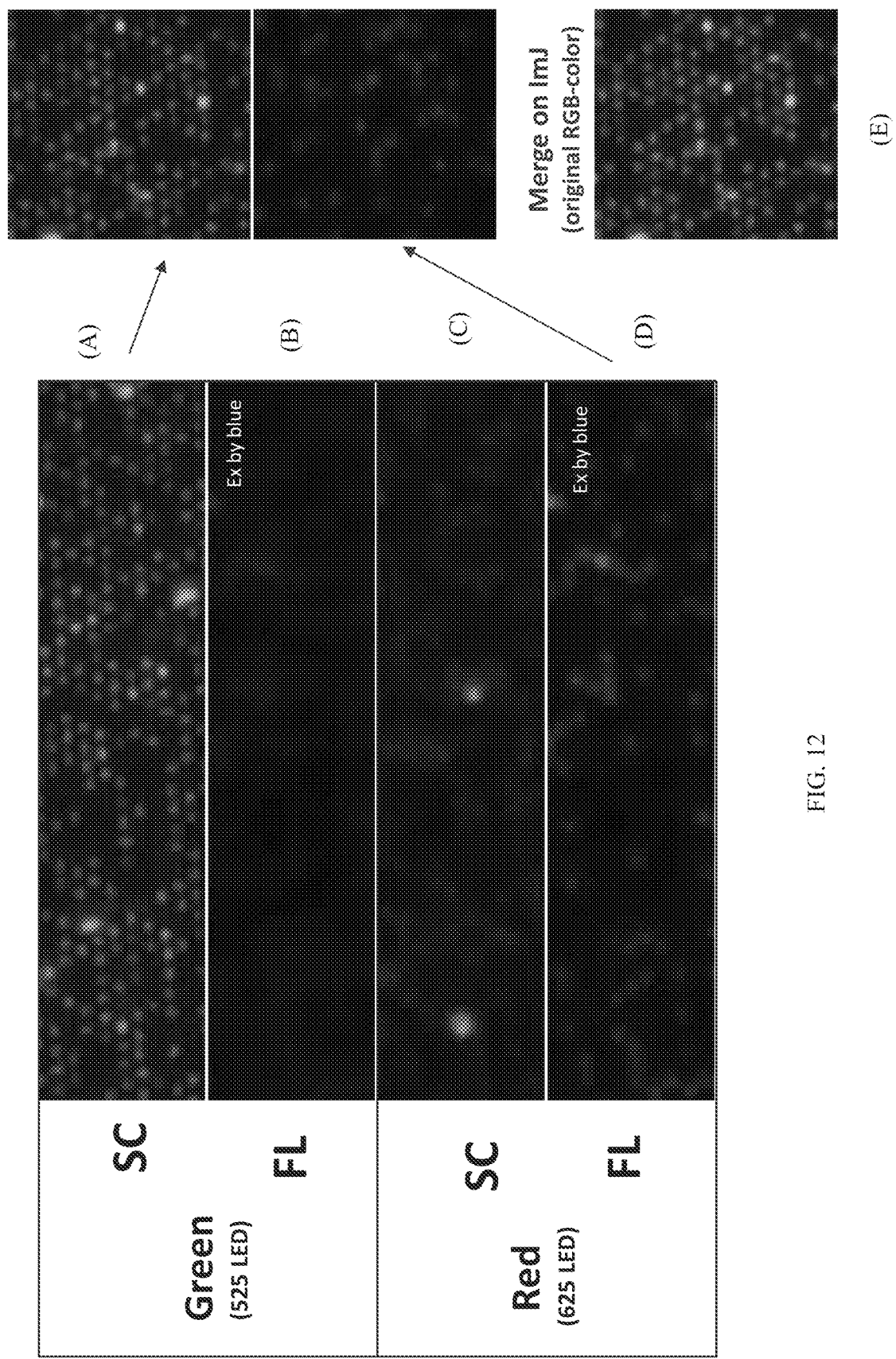
FIG. 12 illustrates images acquired by an optical imaging system illustrated in FIG. 5.

The image analyzer combined the images (A) with (D) that resulted in image (E) as shown in FIG. 12. ImageJ software was used to merge the images (A) and (D). Image (E) illustrates detected positions of "bead-and-fluorescent species" plotted by green and red dots.

Various features and advantages of the invention are set forth in the following claims.

What is claimed is:

1. A method of detecting an analyte of interest in wells comprising:
    (a) contacting a sample suspected of containing an analyte with
        (i) a detection vessel comprising a plurality of wells with at least one bead within a well, wherein the at least one bead comprises a specific binding member that binds to the analyte of interest;
        (ii) a light source configured to emit light toward the detection vessel;
        (iii) a filter positioned to receive and pass through a portion of light reflected that originated from the light source from the at least one bead, and receive and pass through a portion of a fluorescence output from the at least one bead in the detection vessel; and
        (iv) a detector configured to receive a portion of the reflected light and a portion of the fluorescence output that passes through the single filter; and
    (b) determining which wells contain a bead using information from the reflected light and the fluorescence outputs.

2. The method of claim 1, wherein the detection vessel comprises an axis extending therethrough at substantially 90 degrees.

3. The method of claim 2, wherein the light source is positioned at an angle relative to the axis.

4. The method of claim 3, wherein the angle is between 0 degrees and 90 degrees.

5. The method of claim 3, wherein the angle is between 45 degrees and 90 degrees.

6. The method of claim 3, wherein the angle is 80 degrees.

7. The method of claim 2, wherein the light source includes a plurality of light-emitting diodes.

8. The method of claim 1, wherein the light source is a light-emitting diode.

9. The method of claim 1, wherein the light source is comprised of more than one light source.

10. The method of claim 1, wherein the light source is configured to change colors.

11. The method of claim 10, wherein the light source is configured to change between a blue color and a green color.

12. The method of claim 11, wherein the green color light source reflects off at least one bead in the detection vessel for the detector to generate optical data identifying whether a bead is present in the sample.

13. The method of claim 11, wherein the blue color light source excites a bead in the detection vessel for the detector to generate optical data identifying whether an enzyme is present in the sample.

14. The method of claim 1, wherein the fluorescence output is a fluorescence generated after excitation of a bead in the detection vessel by the light source.

* * * * *